(12) United States Patent
Walczak et al.

(10) Patent No.: US 10,093,716 B2
(45) Date of Patent: Oct. 9, 2018

(54) METHODS FOR TREATING CANCER

(71) Applicant: UCL BUSINESS PLC, London (GB)

(72) Inventors: Henning Walczak, London (GB); Silvia Von Karstedt, London (GB)

(73) Assignee: UCL BUSINESS PLC, London (GB)

( * ) Notice: Subject to any disclaimer, the term of this patent is extended or adjusted under 35 U.S.C. 154(b) by 0 days.

(21) Appl. No.: 14/902,966

(22) PCT Filed: Jul. 3, 2014

(86) PCT No.: PCT/GB2014/052025
§ 371 (c)(1),
(2) Date: Jan. 5, 2016

(87) PCT Pub. No.: WO2015/001345
PCT Pub. Date: Jan. 8, 2015

(65) Prior Publication Data
US 2016/0297865 A1    Oct. 13, 2016

(30) Foreign Application Priority Data
Jul. 5, 2013 (GB) .................................. 1312155.3

(51) Int. Cl.
| A61K 38/19 | (2006.01) |
|---|---|
| A61K 39/395 | (2006.01) |
| C07K 14/705 | (2006.01) |
| C07K 16/24 | (2006.01) |
| C07K 16/28 | (2006.01) |
| A61K 38/17 | (2006.01) |
| G01N 33/574 | (2006.01) |
| C07K 14/525 | (2006.01) |
| C07K 14/715 | (2006.01) |
| A61K 39/00 | (2006.01) |

(52) U.S. Cl.
CPC ...... *C07K 14/70575* (2013.01); *A61K 38/177* (2013.01); *A61K 38/191* (2013.01); *A61K 39/3955* (2013.01); *C07K 14/70578* (2013.01); *C07K 16/241* (2013.01); *C07K 16/2875* (2013.01); *G01N 33/57492* (2013.01); *A61K 2039/505* (2013.01); *C07K 14/525* (2013.01); *C07K 14/70596* (2013.01); *C07K 14/7151* (2013.01); *C07K 16/2878* (2013.01); *C07K 16/2896* (2013.01); *C07K 2317/53* (2013.01); *C07K 2317/76* (2013.01); *C07K 2319/30* (2013.01); *G01N 2800/52* (2013.01)

(58) Field of Classification Search
CPC .......... A61K 2300/00; A61K 39/39558; A61K 2039/505; A61K 39/3955; A61K 2039/507; A61K 38/1709; A61K 39/395; A61K 38/16; A61K 38/19; A61K 38/191; C07K 16/30; C07K 2317/76; C07K 2317/565; C07K 16/18; C07K 14/47; C07K 16/24; C07K 16/2896; C07K 16/2866; C07K 14/525
See application file for complete search history.

(56) References Cited

U.S. PATENT DOCUMENTS
7,528,239 B1    5/2009   Rauch et al.

FOREIGN PATENT DOCUMENTS
| EP | 1 396 500 | 3/2004 |
|---|---|---|
| WO | 1998/035986 | 8/1998 |

OTHER PUBLICATIONS

Laguinge et al. DR5 receptor mediates anoikis in human colorectal carcinoma cell lines. Cancer Res 68(3): 909-917, 2008.*
Bhatia et al. Innovative approaches for enhancing cancer gene therapy. Discovery Med 15(84): 309-317, 2013.*
Juengst et al. What next for human gene therapy? Brit Med J 326: 1410-1411, 2003.*
Lemke et al. Getting TRAIL back on track for cancer therapy. Cell Death Diff 21: 1350-1364, 2014.*
Mansoori et al. RNA interference and its role in cancer therapy. Adv Pharm Bull 4(4): 313-321, 2014.*
Mori et al. Distinct function of monoclonal antibody to TRAIL-R2 as potentiator or inhibitor of the ligand TRAIL-induced apoptosis. FEBS Letters 579: 5379-5384, 2005.*
Phillips, A.J. The challenge of gene therapy and DNA delivery. J Pharm Pharmacol 53: 1169-1174, 2001.*
Rubanyi et al. The future of gene therapy. Mol Aspects Med 22: 113-142, 2001.*
Schnepple et al. Isolation of a TRAIL antagonist from the serum of HIV-infected agents. J Biol Chem 286(41): 35742-35754, 2011.*
von Karstedt et al. Cancer cell-autonomous TRAIL-R signaling promotes KRAS-driven cancer progression, invastion, and metastasis. Cancer Cell 27: 561-573, 2015.*
Walczak, H. Death receptor-ligand systems in cancer, cell death, and inflammation. Cold Spring Harbor Perspect Biol 5: a008698, 2013; 18 total pages.*
Yen et al. TRAF-6 dependent signaling pathway is essential for TNF-related apoptosis-inducing ligand (TRAIL) induces osteoclast differentiation. PLOS one 7(6): e38048, Jun. 2012; 10 pages.*
Heins et al. Implications for a newly discovered DR5 specific antagonistic peptide for neurodegenerative diseases. Mol Cell Pharmacol 2(3): 97-100, 2010.*

(Continued)

*Primary Examiner* — Bridget E Bunner
(74) *Attorney, Agent, or Firm* — Andrus Intellectual Property Law, LLP

(57) ABSTRACT

The present invention relates to methods and materials for treating an individual with KRAS-mutated cancer or a cancer in which ROCK is inhibited independently of mutated KRAS. The invention is based on the prevention or disruption of the binding of TRAIL-Receptor to its ligand, TRAIL, in vivo, for example by use of an agent that neutralizes TRAIL and/or a the TRAIL-Receptor (such TRAIL-R2) and/or diminishes TRAIL/TRAIL-Receptor activity, thereby reducing cancer cell transformation, migration and metastasis, prolonging survival of patients.

14 Claims, 8 Drawing Sheets
(6 of 8 Drawing Sheet(s) Filed in Color)

Specification includes a Sequence Listing.

(56) References Cited

OTHER PUBLICATIONS

Morrison et al. Apo2L/TRAIL induction and nuclear translocation of inositol hexakisphosphate kinase 2 during IFN-beta-induced apoptosis in ovarian cancer. Biochem J 385: 595-603, 2005.*
Plasilova et al. TRAIL (Apo2L) suppresses growth of primary human leukemia and myelodysplasia progenitors. Leukemia 16: 67-73 , 2002.*
Bavi, P. et al., "Prognostic significance of TRAIL death receptors in Middle Eastern colorectal carcinomas and their correlation to oncogenic KRAS alterations," (2010) Molecular Cancer 9(1):203-208.
Hoogwater, F.J. H. et al., "Oncogenic K-Ras turns death receptors into metastasis-promoting receptors in human and mouse colorectal cancer cells," (2010) Gastroenterology 138(7):2357-2367.
Huang, S. et al., "Lung-cancer chemoprevention by induction of synthetic lethality in mutant KRAS premalignant cells In Vitro and In Vivo," (2011) Cancer Prev. Res. 4:666-673.
Merino, D. et al., "Differential inhibition of TRAIL-mediated DR5-DISC formation by decoy receptors 1 and 2," (2006) Molecular and Cellular Biology 26(19):7046-7055.
Oikonomou, E. et al., "TRAIL receptor upregulation and the implication of KRAS/BRAF mutations in human colon cancer tumors," (2009) Int. J. Cancer 125:2127-2135.
Sahu, R.P. et al., "The role of K-Ras gene mutation in TRAIL-induced apoptosis in pancreatic and lung cancer cell lines," (2011) Cancer Chemother. Pharmacol. 67:481-487.
International Search Report and Written Opinion for International Patent Application No. PCT/GB2014/052025 dated Oct. 30, 2014 (16 pages).

* cited by examiner

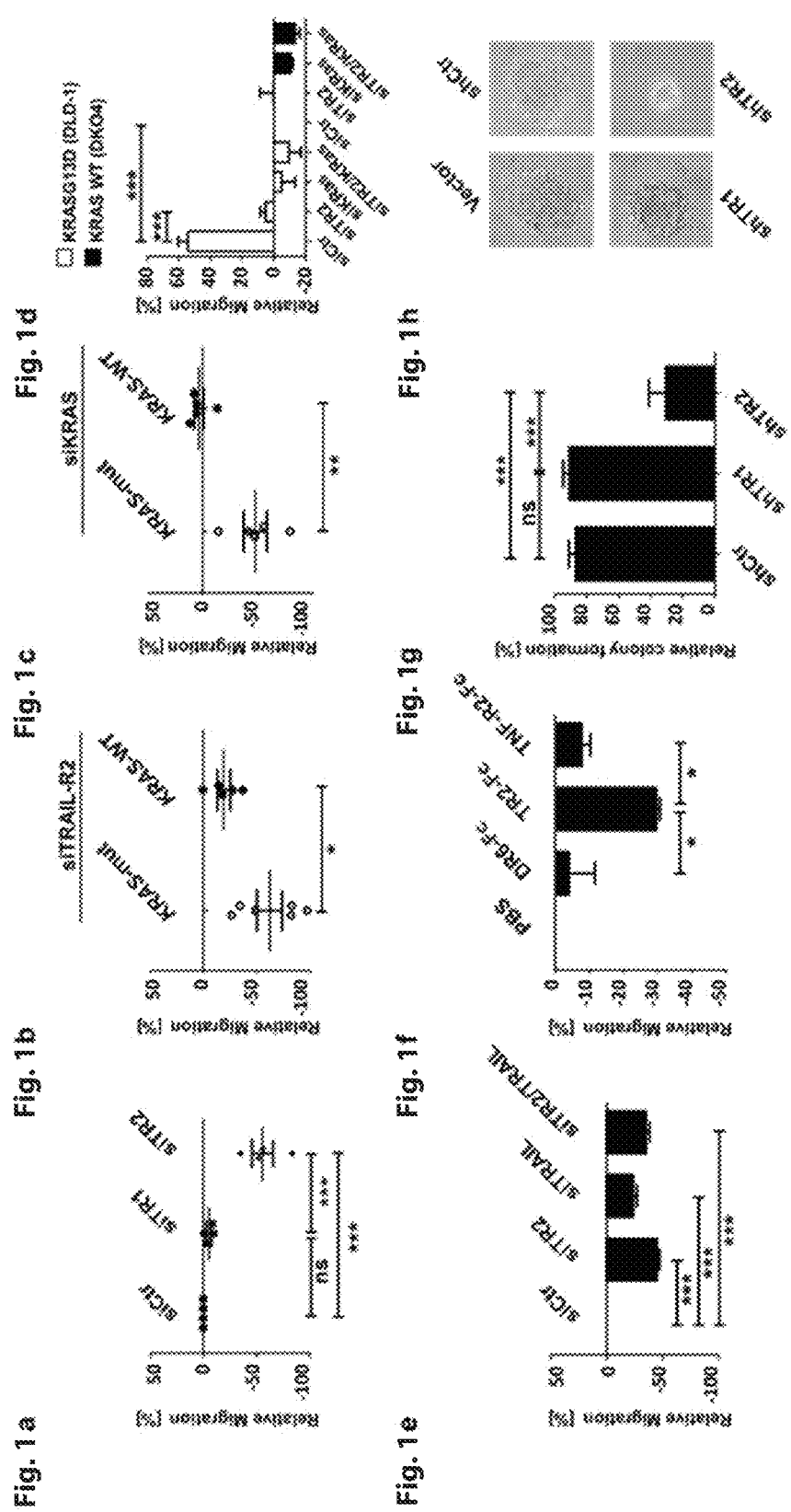

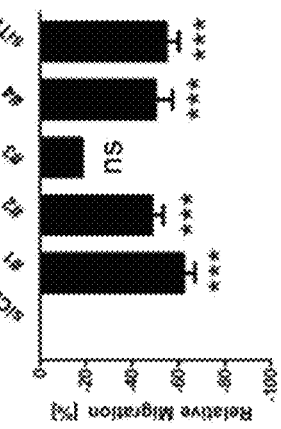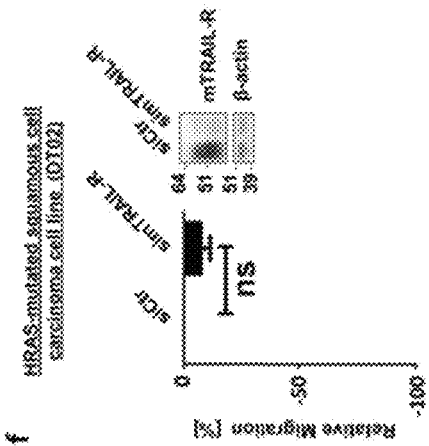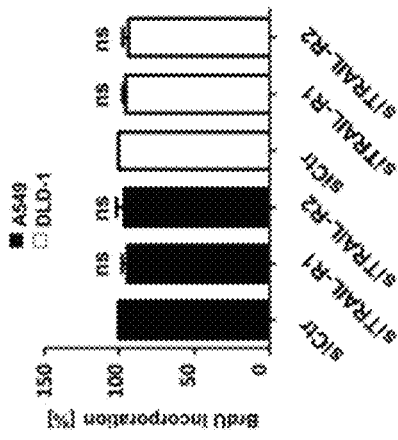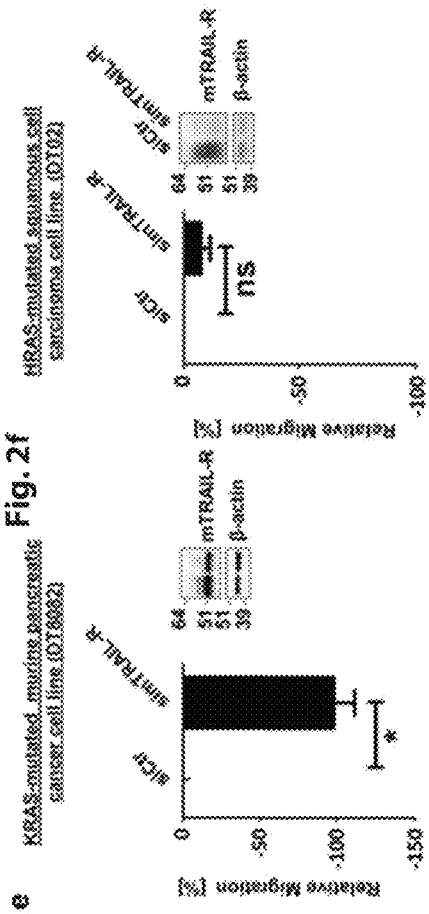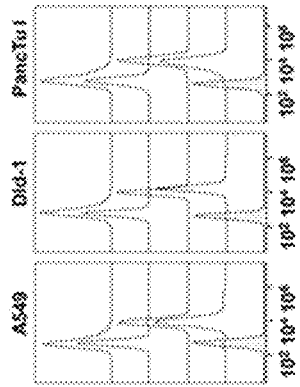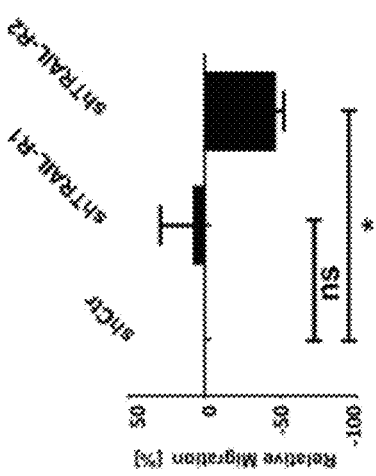
Fig. 2a  Fig. 2b  Fig. 2c
Fig. 2d  Fig. 2e  Fig. 2f

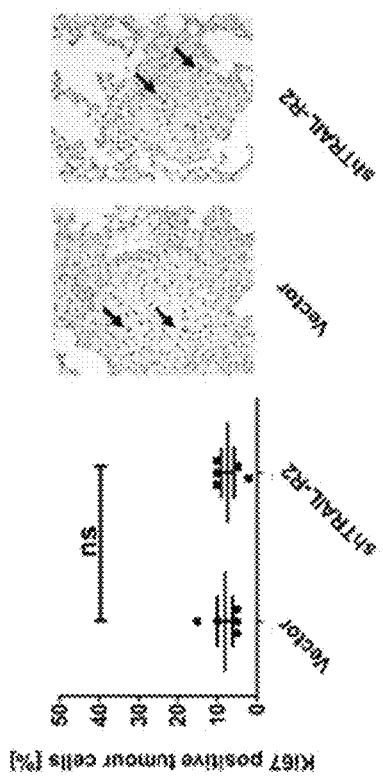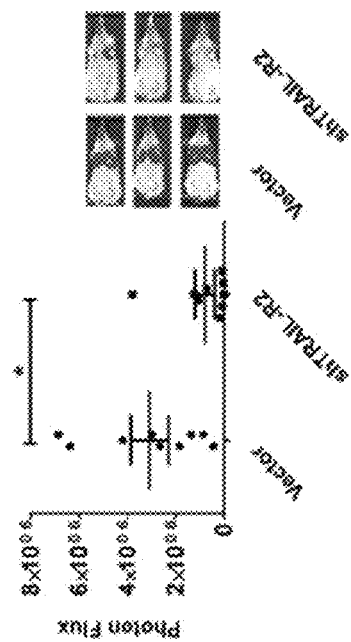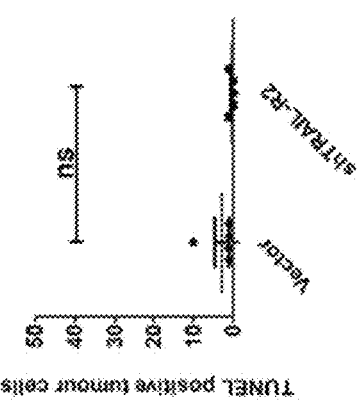

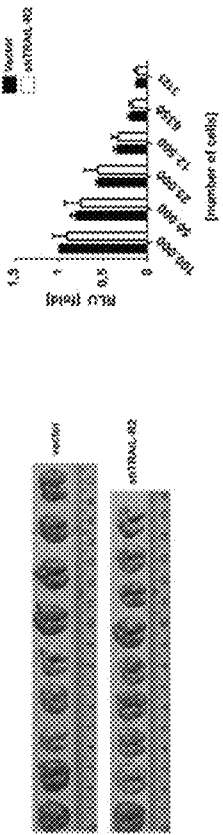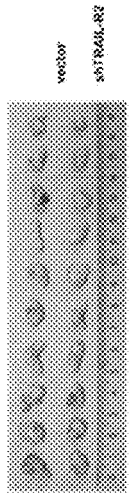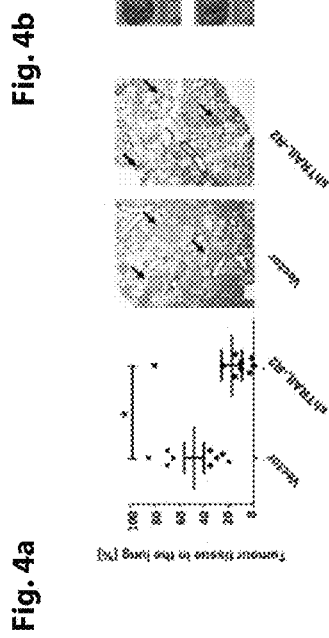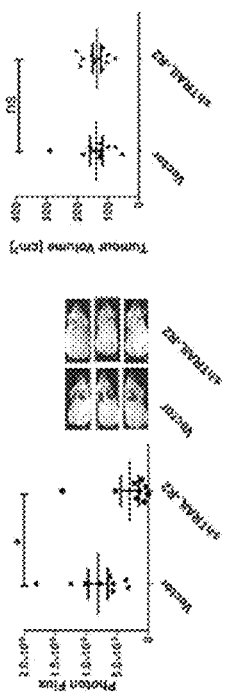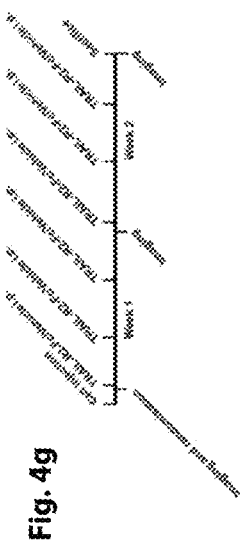
Fig. 4a  Fig. 4b  Fig. 4c  Fig. 4d  Fig. 4e  Fig. 4f  Fig. 4g

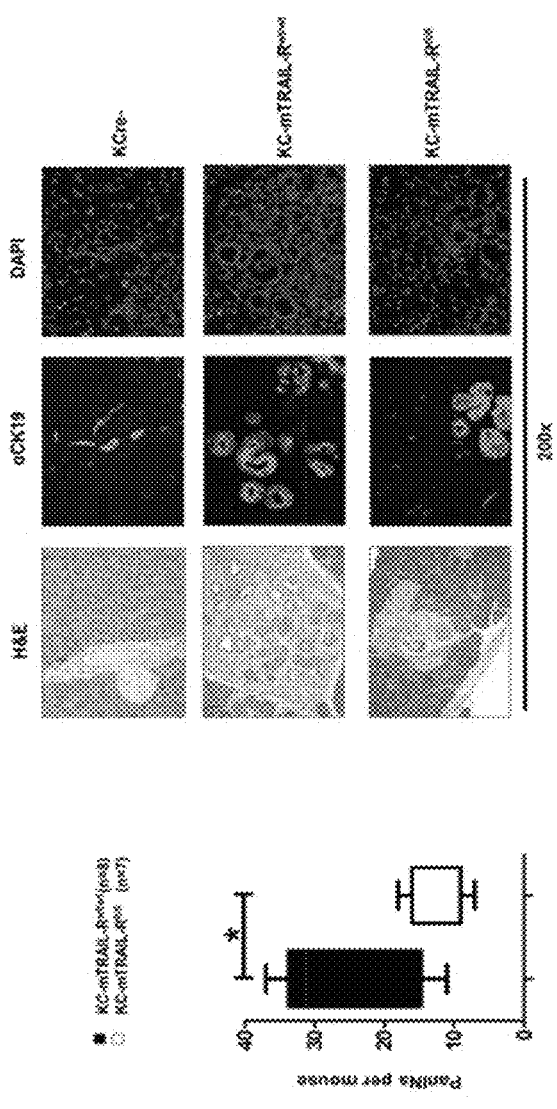
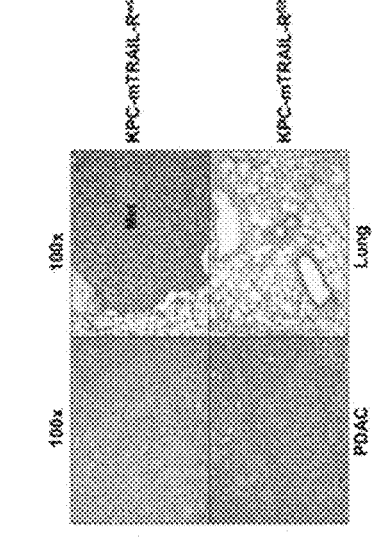
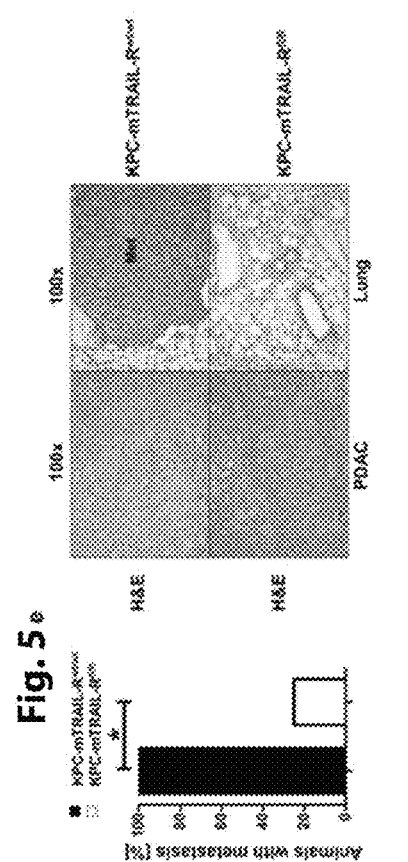
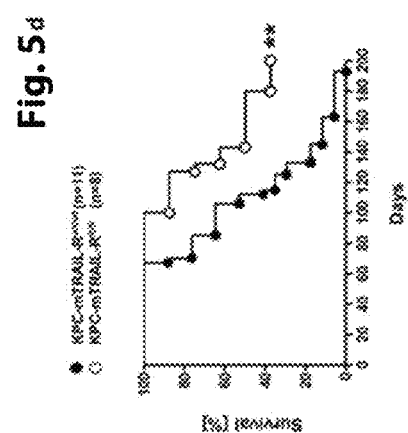
Fig. 5a, Fig. 5b, Fig. 5c, Fig. 5d, Fig. 5e

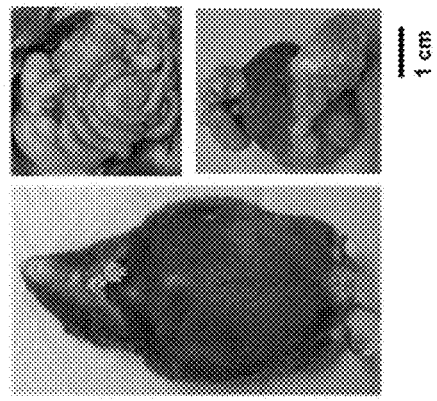
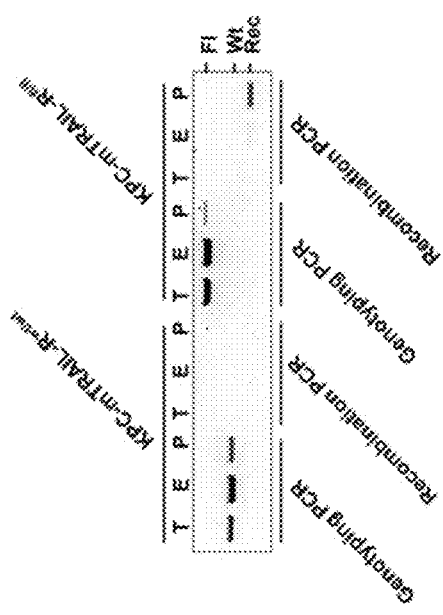
Fig. 6a
Fig. 6b
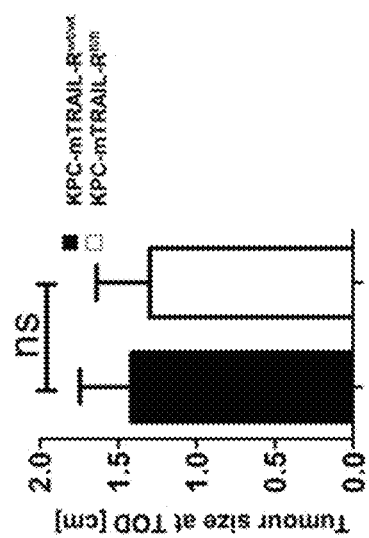
Fig. 6c

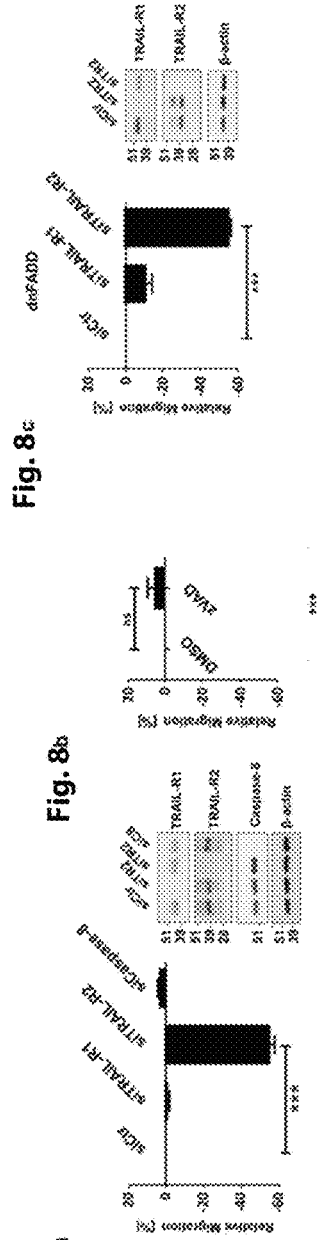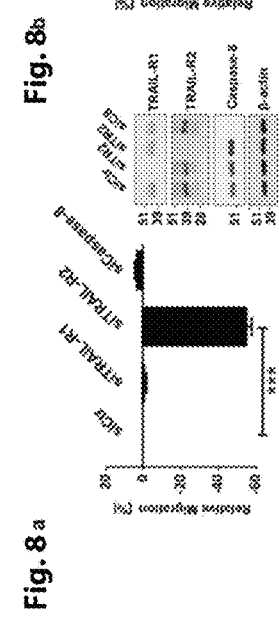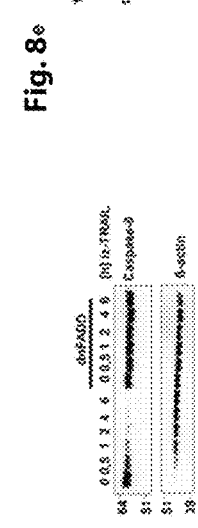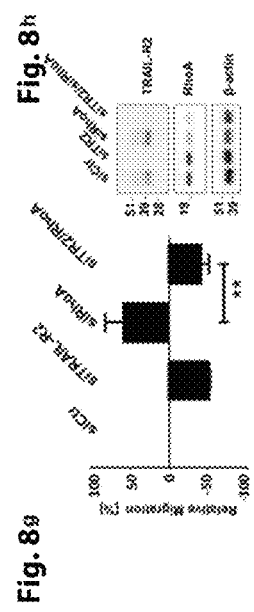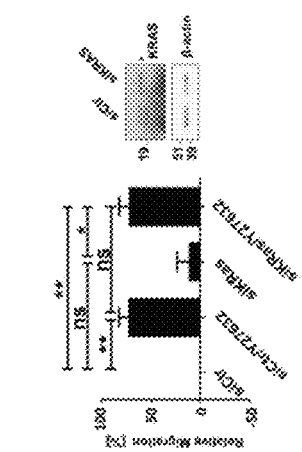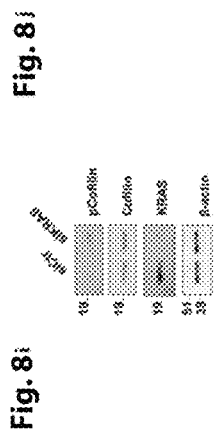

SEQUENCE LISTING

```
<160> NUMBER OF SEQ ID NOS: 16

<210> SEQ ID NO 1
<211> LENGTH: 57
<212> TYPE: DNA
<213> ORGANISM: Artificial sequence
<220> FEATURE:
<223> OTHER INFORMATION: Synthetic sequence: shTRAIL-R1

<400> SEQUENCE: 1
ccggcttagg tgttaggagt taatactcga gtattaactc ctaacaccta agttttt         57

<210> SEQ ID NO 2
<211> LENGTH: 57
<212> TYPE: DNA
<213> ORGANISM: Artificial sequence
<220> FEATURE:
<223> OTHER INFORMATION: Synthetic sequence: shTRAIL-R2

<400> SEQUENCE: 2
ccgggcagaa gattgaggac cacttctcga gaagtggtcc tcaatcttct gctttt         57

<210> SEQ ID NO 3
<211> LENGTH: 38
<212> TYPE: DNA
<213> ORGANISM: Artificial sequence
<220> FEATURE:
<223> OTHER INFORMATION: Synthetic sequence: Primer

<400> SEQUENCE: 3
ccagggactc ctgcctcttg tgacaaaact cacacatg                             38

<210> SEQ ID NO 4
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 4
tatagaattc tcatttaccc ggagacaggg                                      30

<210> SEQ ID NO 5
<211> LENGTH: 40
```

```
<212> TYPE: DNA
<213> ORGANISM: Artificial sequence
<220> FEATURE:
<223> OTHER INFORMATION: Synthetic sequence: Primer
<220> FEATURE:
<221> NAME/KEY: misc_feature
<222> LOCATION: (29)..(29)
<223> OTHER INFORMATION: 'n' is disclosed as 'e'

<400> SEQUENCE: 5
tataaagctt gccgccacca tggaacaang gggacagaac                    40

<210> SEQ ID NO 6
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 6
gtgagttttg tcacaagagg caggagtccc tgg                           33

<210> SEQ ID NO 7
<211> LENGTH: 40
<212> TYPE: DNA
<213> ORGANISM: Artificial sequence
<220> FEATURE:
<223> OTHER INFORMATION: Synthetic sequence: Primer

<400> SEQUENCE: 7
tataaagctt gccgccacca tggaacaacg gggacagaac                    40

<210> SEQ ID NO 8
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 8
tatagaattc tcatttaccc ggagacaggg                               30

<210> SEQ ID NO 9
<211> LENGTH: 440
<212> TYPE: PRT
<213> ORGANISM: Homo sapiens

<400> SEQUENCE: 9
```

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro

```
            115                 120                 125
Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
    370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
        435                 440

<210> SEQ ID NO 10
<211> LENGTH: 1859
<212> TYPE: DNA
<213> ORGANISM: Homo sapiens
<220> FEATURE:
<221> NAME/KEY: CDS
<222> LOCATION: (145)..(1467)

<400> SEQUENCE: 10
gaattcgcgg caccgctcat aaatcagcac gcggccggag aaccccgcaa tctttgcgcc    60
cacaaaatac accgacgatg cccgatctac tttaagggct gaaacccacg ggcctgagag   120
actataagag cgttccctac cgcc atg gaa caa cgg gga cag aac gcc ccg      171
                          Met Glu Gln Arg Gly Gln Asn Ala Pro
```

```
gcc gct tcg ggg gcc cgg aaa agg cac ggc cca gga ccc agg gag gcg    219
Ala Ala Ser Gly Ala Arg Lys Arg His Gly Pro Gly Pro Arg Glu Ala
10              15                  20                  25 cgg gga gcc agg cct ggg ccc cgg gtc ccc aag acc ctt gtg ctc gtt    267
Arg Gly Ala Arg Pro Gly Pro Arg Val Pro Lys Thr Leu Val Leu Val
                30                  35                  40 gtc gcc gcg gtc ctg ctg ttg gtc tca gct gag tct gct ctg atc acc    315
Val Ala Ala Val Leu Leu Leu Val Ser Ala Glu Ser Ala Leu Ile Thr
            45                  50                  55 caa caa gac cta gct ccc cag cag aga gcg gcc cca caa caa aag agg    363
Gln Gln Asp Leu Ala Pro Gln Gln Arg Ala Ala Pro Gln Gln Lys Arg
        60                  65                  70 tcc agc ccc tca gag gga ttg tgt cca cct gga cac cat atc tca gaa    411
Ser Ser Pro Ser Glu Gly Leu Cys Pro Pro Gly His His Ile Ser Glu
75                  80                  85 gac ggt aga gat tgc atc tcc tgc aaa tat gga cag gac tat agc act    459
Asp Gly Arg Asp Cys Ile Ser Cys Lys Tyr Gly Gln Asp Tyr Ser Thr
90                  95                  100                 105 cac tgg aat gac ctc ctt ttc tgc ttg cgc tgc acc agg tgt gat tca    507
His Trp Asn Asp Leu Leu Phe Cys Leu Arg Cys Thr Arg Cys Asp Ser
                110                 115                 120 ggt gaa gtg gag cta agt ccg tgc acc acg acc aga aac aca gtg tgt    555
Gly Glu Val Glu Leu Ser Pro Cys Thr Thr Thr Arg Asn Thr Val Cys
            125                 130                 135 cag tgc gaa gaa ggc acc ttc cgg gaa gaa gat tct cct gag atg tgc    603
Gln Cys Glu Glu Gly Thr Phe Arg Glu Glu Asp Ser Pro Glu Met Cys
        140                 145                 150 cgg aag tgc cgc aca ggg tgt ccc aga ggg atg gtc aag gtc ggt gat    651
Arg Lys Cys Arg Thr Gly Cys Pro Arg Gly Met Val Lys Val Gly Asp
155                 160                 165 tgt aca ccc tgg agt gac atc gaa tgt gtc cac aaa gaa tca ggt aca    699
Cys Thr Pro Trp Ser Asp Ile Glu Cys Val His Lys Glu Ser Gly Thr
170                 175                 180                 185 aag cac agt ggg gaa gcc cca gct gtg gag gag acg gtg acc tcc agc    747
Lys His Ser Gly Glu Ala Pro Ala Val Glu Glu Thr Val Thr Ser Ser
                190                 195                 200 cca ggg act cct gcc tct ccc tgt tct ctc tca ggc atc atc ata gga    795
Pro Gly Thr Pro Ala Ser Pro Cys Ser Leu Ser Gly Ile Ile Ile Gly
            205                 210                 215 gtc aca gtt gca gcc gta gtc ttg att gtg gct gtg ttt gtt tgc aag    843
Val Thr Val Ala Ala Val Val Leu Ile Val Ala Val Phe Val Cys Lys
        220                 225                 230 tct tta ctg tgg aag aaa gtc ctt cct tac ctg aaa ggc atc tgc tca    891
Ser Leu Leu Trp Lys Lys Val Leu Pro Tyr Leu Lys Gly Ile Cys Ser
235                 240                 245 ggt ggt ggt ggg gac cct gag cgt gtg gac aga agc tca caa cga cct    939
Gly Gly Gly Gly Asp Pro Glu Arg Val Asp Arg Ser Ser Gln Arg Pro
250                 255                 260                 265 ggg gct gag gac aat gtc ctc aat gag atc gtg agt atc ttg cag ccc    987
Gly Ala Glu Asp Asn Val Leu Asn Glu Ile Val Ser Ile Leu Gln Pro
                270                 275                 280 acc cag gtc cct gag cag gaa atg gaa gtc cag gag cca gca gag cca   1035
Thr Gln Val Pro Glu Gln Glu Met Glu Val Gln Glu Pro Ala Glu Pro
            285                 290                 295 aca ggt gtc aac atg ttg tcc ccc ggg gag tca gag cat ctg ctg gaa   1083
Thr Gly Val Asn Met Leu Ser Pro Gly Glu Ser Glu His Leu Leu Glu
        300                 305                 310 ccg gca gaa gct gaa agg tct cag agg agg agg ctg ctg gtt cca gca   1131
```

```
                                              Pro Ala Glu Ala Glu Arg Ser Gln Arg Arg Arg Leu Leu Val Pro Ala
                                                  315                 320                 325 aat gaa ggt gat ccc act gag act ctg aga cag tgc ttc gat gac ttt        1179
Asn Glu Gly Asp Pro Thr Glu Thr Leu Arg Gln Cys Phe Asp Asp Phe
330                 335                 340                 345 gca gac ttg gtg ccc ttt gac tcc tgg gag ccg ctc atg agg aag ttg        1227
Ala Asp Leu Val Pro Phe Asp Ser Trp Glu Pro Leu Met Arg Lys Leu
                350                 355                 360 ggc ctc atg gac aat gag ata aag gtg gct aaa gct gag gca gcg ggc        1275
Gly Leu Met Asp Asn Glu Ile Lys Val Ala Lys Ala Glu Ala Ala Gly
            365                 370                 375 cac agg gac acc ttg tac acg atg ctg ata aag tgg gtc aac aaa acc        1323
His Arg Asp Thr Leu Tyr Thr Met Leu Ile Lys Trp Val Asn Lys Thr
        380                 385                 390 ggg cga gat gcc tct gtc cac acc ctg ctg gat gcc ttg gag acg ctg        1371
Gly Arg Asp Ala Ser Val His Thr Leu Leu Asp Ala Leu Glu Thr Leu
    395                 400                 405 gga gag aga ctt gcc aag cag aag att gag gac cac ttg ttg agc tct        1419
Gly Glu Arg Leu Ala Lys Gln Lys Ile Glu Asp His Leu Leu Ser Ser
410                 415                 420                 425 gga aag ttc atg tat cta gaa ggt aat gca gac tct gcc atg tcc taa        1467
Gly Lys Phe Met Tyr Leu Glu Gly Asn Ala Asp Ser Ala Met Ser
                430                 435                 440 gtgtgattct cttcaggaag tgagaccttc cctggtttac ctttttttctg gaaaaagccc     1527 aactggactc cagtcagtag gaaagtgcca caattgtcac atgaccggta ctggaagaaa     1587
ctctcccatc caacatcacc cagtggatgg aacatcctgt aacttttcac tgcacttggc     1647 attatttttta taagctgaat gtgataataa ggacactatg gaaatgtctg gatcattccg     1707
tttgtgcgta ctttgagatt tggtttggga tgtcattgtt ttcacagcac ttttttatcc     1767
taatgtaaat gctttattta tttatttggg ctacattgta agatccagca ggtcgtctcg     1827
tttcaagatc tgtttaaact agttagctag gc                                    1859

<210> SEQ ID NO 11
<211> LENGTH: 440
<212> TYPE: PRT
<213> ORGANISM: Homo sapiens

<400> SEQUENCE: 11

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140
```

```
Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
        435                 440

<210> SEQ ID NO 12
<211> LENGTH: 846
<212> TYPE: DNA
<213> ORGANISM: Homo sapiens

<400> SEQUENCE: 12
atggctatga tggaggtcca gggggggaccc agcctgggac agacctgcgt gctgatcgtg     60
atcttcacag tgctcctgca gtctctctgt gtggctgtaa cttacgtgta ctttaccaac    120
gagctgaagc agatgcagga caagtactcc aaaagtggca ttgcttgttt cttaaaagaa    180
gatgacagtt attgggaccc caatgacgaa gagagtatga cagcccctg ctggcaagtc    240 aagtggcaac tccgtcagct cgttagaaag atgattttga gaacctctga ggaaaccatt    300
tctacagttc aagaaaagca acaaaatatt tctcccctag tgagagaaag aggtcctcag    360
agagtagcag ctcacataac tgggaccaga ggaagaagca acacattgtc ttctccaaac    420
```

-continued

```
tccaagaatg aaaaggctct gggccgcaaa ataaactcct gggaatcatc aaggagtggg    480
cattcattcc tgagcaactt gcacttgagg aatggtgaac tggtcatcca tgaaaaggg     540 ttttactaca tctattccca aacatacttt cgatttcagg aggaaataaa agaaaacaca    600
aagaacgaca aacaaatggt ccaatatatt tacaaataca caagttatcc tgaccctata    660
ttgttgatga aaagtgctag aaatagttgt tggtctaaag atgcagaata tggactctat    720
tccatctatc aagggggaat atttgagctt aaggaaaatg acagaatttt tgtttctgta    780
acaaatgagc acttgataga catggaccat gaagccagtt ttttcggggc cttttagtt     840 ggttaa                                                               846
```

<210> SEQ ID NO 13
<211> LENGTH: 281
<212> TYPE: PRT
<213> ORGANISM: Homo sapiens

<400> SEQUENCE: 13

```
Met Ala Met Met Glu Val Gln Gly Gly Pro Ser Leu Gly Gln Thr Cys
1               5                   10                  15

Val Leu Ile Val Ile Phe Thr Val Leu Gln Ser Leu Cys Val Ala
                20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

```
<210> SEQ ID NO 14
<211> LENGTH: 6
<212> TYPE: PRT
<213> ORGANISM: Homo sapiens

<400> SEQUENCE: 14

Ile Thr Gln Gln Asp Leu
1               5

<210> SEQ ID NO 15
<211> LENGTH: 435
<212> TYPE: PRT
<213> ORGANISM: Artificial sequence
<220> FEATURE:
<223> OTHER INFORMATION: Synthetic sequence: Amino acid sequence of the
      TRAIL-R2-Fc protein

<400> SEQUENCE: 15

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
                180                 185                 190

Ala Val Glu Glu Thr Val Thr Ser Ser Pro Gly Thr Pro Ala Ser Cys
            195                 200                 205

Asp Lys Thr His Thr Cys Pro Pro Cys Pro Ala Pro Glu Leu Leu Gly
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
                260                 265                 270

His Asn Ala Lys Thr Lys Pro Arg Glu Glu Gln Tyr Asn Ser Thr Tyr
            275                 280                 285

Arg Val Val Ser Val Leu Thr Val Leu His Gln Asp Trp Leu Asn Gly
    290                 295                 300
```

| | | | | | | | | | | | | |
|---|---|---|---|---|---|---|---|---|---|---|---|---|
|Lys|Glu|Tyr|Lys|Cys|Lys|Val|Ser|Asn|Lys|Ala|Leu|Pro|Ala|Pro|Ile|
|305| | | |310| | | |315| | | |320|

Glu Lys Thr Ile Ser Lys Ala Lys Gly Gln Pro Arg Glu Pro Gln Val
            325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
            355                 360                 365

Trp Glu Ser Asn Gly Gln Pro Glu Asn Asn Tyr Lys Thr Thr Pro Pro
370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
            405                 410                 415

His Glu Ala Leu His Asn His Tyr Thr Gln Lys Ser Leu Ser Leu Ser
            420                 425                 430

Pro Gly Lys
      435

<210> SEQ ID NO 16
<211> LENGTH: 1308
<212> TYPE: DNA
<213> ORGANISM: Artificial sequence
<220> FEATURE:
<223> OTHER INFORMATION: Synthetic sequence: Nucleotide sequence
      encoding the immature TRAIL-R2-Fc protein

<400> SEQUENCE: 16

```
atggaacaac ggggacagaa cgccccggcc gcttcggggg cccggaaaag gcacggccca      60
ggacccaggg aggcgcgggg agccaggcct gggccccggg tccccaagac ccttgtgctc     120
gttgtcgccg cggtcctgct gttggtctca gctgagtctg ctctgatcac caacaagac     180 ctagctcccc agcagagagc ggccccacaa caaaagaggt ccagcccctc agagggattg     240
tgtccacctg gacaccatat ctcagaagac ggtagagatt gcatctcctg caaatatgga     300
caggactata gcactcactg gaatgacctc ctttttctgct tgcgctgcac caggtgtgat     360
tcaggtgaag tggagctaag tccctgcacc acgaccagaa acacagtgtg tcagtgcgaa     420
gaaggcacct tccgggaaga agattctcct gagatgtgcc ggaagtgccg cacagggtgt     480
cccagaggga tggtcaaggt cggtgattgt acaccctgga gtgacatcga atgtgtccac     540
aaagaatcag gtacaaagca cagtggggaa gtcccagctg tggaggagac ggtgacctcc     600
agcccaggga ctcctgcctc ttgtgacaaa actcacacat gcccaccgtg cccagcacct     660
gaactcctgg gggaccgtc agtcttcctc ttccccccaa aacccaagga caccctcatg     720
atctcccgga cccctgaggt cacatgcgtg gtggtggacg tgagccacga agaccctgag     780
gtcaagttca actggtacgt ggacggcgtg gaggtgcata atgccaagac aaagccgcgg     840
gaggagcagt acaacagcac gtaccgtgtg gtcagcgtcc tcaccgtcct gcaccaggac     900
tggctgaatg gcaaggagta caagtgcaag gtctccaaca aagccctccc agcccccatc     960
gagaaaacca tctccaaagc caaagggcag ccccgagaac cacaggtgta caccctgccc    1020
ccatcccggg atgagctgac caagaaccag gtcagcctga cctgcctggt caaaggcttc    1080
tatcccagcg acatcgccgt ggagtgggag agcaatgggc agccggagaa caactacaag    1140
accacgcctc ccgtgctgga ctccgacggc tccttcttcc tctacagcaa gctcaccgtg    1200
```

```
gacaagagca ggtggcagca ggggaacgtc ttctcatgct ccgtgatgca tgaggctctg    1260
cacaaccact acacgcagaa gagcctctcc ctgtctccgg gtaaatga                 1308
```

METHODS FOR TREATING CANCER

CROSS-REFERENCE TO RELATED APPLICATIONS

This patent application is a national stage filing under 35 U.S.C. 371 of International Application No. PCT/GB2014/052025, filed Jul. 3, 2014, which claims the benefit of priority of Great Britain Application No. GB1312155.3, filed Jul. 5, 2013, both of which are incorporated herein by reference in their entireties.

SEQUENCE LISTING

This application was filed electronically via EFS-Web and includes an electronically submitted Sequence Listing in .txt format. The .txt file contains a sequence listing entitled "2016-01-05_5659-00028_Sequence_Listing_as_Filed.txt" created on Dec. 21, 2015 and is 26,149 bytes in size. The Sequence Listing contained in this .txt file is part of the specification and is hereby incorporated by reference herein in its entirety.

FIELD OF INVENTION

The present invention relates to methods for treating an individual with KRAS-mutated cancer or a cancer in which ROCK is inhibited independently of mutated KRAS by preventing or disrupting the binding of TRAIL-R2 to its ligand, TRAIL, in vivo, whereupon that neutralization of TRAIL and/or TRAIL-R2 activity reduces cancer cell transformation, migration and metastasis, prolonging survival of patients.

BACKGROUND

The Tumour Necrosis Factor (TNF) superfamily member TNF-related apoptosis-inducing ligand (TRAIL) can selectively induce apoptosis in a wide variety of tumour cells in vivo without causing toxicity to normal cells (Ashkenazi et al., 1999; Walczak et al., 1999). Consequently, these findings have triggered the design of TRAIL-receptor (TRAIL-R) agonistic cancer therapies (WO 2002094880 A1, U.S. Pat. No. 7,915,245 B2). Yet, in recent years it has become apparent that human primary tumour cells are often resistant to TRAIL-mediated apoptosis (Todaro et al., 2008) and that TRAIL can also induce non-apoptotic signalling in cancer cells (Azijli et al., 2013; Newsom-Davis et al., 2009). Moreover, in many cancers the death-domain-containing TRAIL-Rs, i.e. TRAIL-R1 (Pan et al., 1997) (also known as DR4) and TRAIL-R2 (Walczak et al., 1997) (also known as KILLER, DR5, TRICK2A/TRICK2B, Apo2), the two apoptosis-inducing receptors for TRAIL, are expressed at higher levels than in normal tissue (Daniels et al., 2005; Ozawa et al., 2001; Spierings et al., 2003). Considering that these two receptors serve as therapeutic targets for agonists whose purpose it is to induce apoptosis, it seemed an advantageous coincidence that these receptors were expressed at higher levels in many cancers than in normal tissue. However, this observation also raised the question whether there could be a yet unknown and unexplored benefit for cancers to highly express these TRAIL-Rs.

In an earlier study, it was shown in a DMBA/TPA-induced mouse model of skin cancer that is typically driven by oncogenic mutations of the Harvey rat sarcoma viral oncogene homologue (HRAS), that murine TRAIL-R (mTRAIL-R) acts as a specific suppressor of lymph node metastases. The proposed mechanism for this effect was induction of cell death via mTRAIL-R following detachment of the cancer cells from the primary tumour (Grosse-Wilde et al., 2008). Conversely, in another study to which one of us (H.W.) also contributed it was shown that human and murine colorectal cancer cell lines in which the Kirsten rat sarcoma viral oncogene homologue (KRAS) is oncogenically mutated were not only resistant to TRAIL- and CD95L-mediated apoptosis induction but that stimulation by these ligands increased motility and membrane ruffling in these cells (Hoogwater et al., 2010). The conclusion of that study was that patients with KRAS-mutated cancers should not be treated with TRAIL-R agonists (Hoogwater et al., 2010).

Oncogenic mutation of KRAS is very frequent in pancreatic cancer (Hidalgo, 2010; Jaffee et al., 2002), frequent in colon (Grady and Markowitz, 2002) and lung cancer (Mitsuuchi and Testa, 2002) and also occurs, albeit at much lower frequencies, in other cancer types such as biliary tract malignancies, endometrial cancer (Ito et al., 1996), cervical cancer (Wegman et al., 2011), bladder cancer (Przybojewska et al., 2000), liver cancer and cholangiocarcinoma (Boix-Ferrero et al., 2000), myeloid leukemia (Ahmad et al., 2009) and breast cancer (Karnoub and Weinberg, 2008). These are some of the most aggressive human cancers and despite many efforts to design efficient therapies for them, survival rates of patients with cancers that bear oncogenic KRAS mutations are still very low. In some cases oncogenic mutation of KRAS is even an exclusion criterion for treatment by certain drugs because they have been found to be ineffective in these patients (Amado et al., 2008; Deschoolmeester et al., 2010; Karapetis et al., 2008; van Krieken et al., 2008). The aggressive behaviour of KRAS-mutated cancers can be attributed to their inherent chemoresistance, strong invasiveness and capacity to metastasize (Downward, 2003), traits which render these cancers very difficult to treat (Chaffer and Weinberg, 2011). However, the effector mechanisms mediating invasiveness and metastasis of KRAS-mutated cancers are only incompletely understood and, importantly, have so far escaped therapeutic intervention.

It will be appreciated from the forgoing that the provision of methods and materials directed to the treatment of KRAS-mutated cancers, or cancers in which similar pathological pathways or mechanisms are present, would provide a useful contribution to the art

DISCLOSURE OF THE INVENTION

Here we show that oncogenic KRAS relies on the interaction of endogenous TRAIL with endogenous TRAIL-R2 for transformation and metastasis, identifying TRAIL/TRAIL-R2 signalling as a novel effector mechanism required for KRAS-driven transformation and metastasis. The signal that is responsible for the pro-tumourigenic effects of crosslinking of endogenous TRAIL-R2 by endogenous TRAIL is not generated via FADD and Caspase-8, the canonical signalling molecules of the death-domain-containing TRAIL-Rs that are required for apoptosis induction by these receptors, and it also does not require caspase activity. Instead, we found that oncgenically mutated KRAS inhibits ROCK which, in turn enables activation of Rac1 downstream of TRAIL/TRAIL-R2.

Thus, in the light of the disclosure herein it can be seen that other oncogenic alterations that result in inhibition of ROCK can also enable TRAIL/TRAIL-R-mediated Rac1 activation. Besides mutated KRAS, integrin signalling through Src and FAK (Ahn et al., 2010), BRAF (Klein et al., 2008), Raf-1 (Ehrenreiter et al., 2009) and Notch3 (Belin de Chantemele et al., 2008) have been linked to ROCK inhibition. Therefore, cancers that present with aberrant signalling in the above named pathways may also employ the TRAIL/TRAIL-R2 system for enhanced migration and metastasis and should therefore also be considered for the therapies put forward here, i.e. the inhibition of TRAIL, of TRAIL-R2, and/or inhibition of TRAIL/TRAIL-R2 pro-migratory activity.

One way to achieve this inhibition is by interfering with the interaction of TRAIL with TRAIL-R2. One preferred way of achieving this is with a biotherapeutic drug that binds and inhibits TRAIL or a biotherapeutic drug that binds to TRAIL-R2 and neutralises it. This can be achieved by the biotherapeutic drug inhibiting the interaction of TRAIL with TRAIL-R2 but it may also be achieved without inhibiting this interaction. Preferably these drugs are of fully human origin. Alternatively, drugs could be employed that interfere with the intracellular signalling of TRAIL/TRAIL-R2 that mediates pro-tumourigenic effects. This could e.g. be achieved with inhibitors of Rac1 activity.

The present invention provides a method for treating an individual suffering from KRAS-mutated cancer, or a cancer in which ROCK is inhibited, with e.g.:
  an agent that neutralizes TRAIL,
  an agent that neutralises TRAIL-R2 (or other TRAIL-R described herein) and/or
  an agent that interferes with the pro-tumourigenic activity triggered by TRAIL and/or TRAIL-R2 (or other TRAIL-R described herein).

"Neutralises" in this context will be understood to mean modulates a biological activity of, either directly (for example by binding to the relevant target) or indirectly. As used herein, the term "biological activity" means any observable effect resulting from the interaction between the protein\receptor (binding partners). Typically the effect will be one causally related to cancer cell transformation, migration and metastasis. Representative, but non-limiting, examples of biological activity in the context of the present invention include signalling and regulation of the genes discussed herein e.g. oncogenic KRAS. Suitable systems for identifying and confirming the effects of such agents are described below, as are relevant biological activities.

For example, according to a preferred embodiment of the invention, the agent neutralising TRAIL and/or TRAIL-R2 activity reduces the activation state of Rac1 in KRAS-mutated cells. According to the present invention, TRAIL activity on TRAIL-R2 can be determined by a person trained at the use of a suitable assay as outlined in example 1 (FIG. 7).

"Neutralises" does not imply complete inactivation. The modulation is generally inhibition i.e. a reduction or diminution in the relevant biological activity by comparison with the activity seen in the absence of the agent.

For brevity below, when TRAIL-Rs are discussed, the preferred embodiment of TRAIL-R2 may be specifically referred to. Nevertheless it will be appreciated that all such discussion applies mutatis mutandis to any other TRAIL-R—for example TRAIL-R1, TRAIL-R3, TRAIL-R4 or OPG.

Thus according to one aspect of the invention there is provided the use of agents that decrease the biological activity TRAIL or TRAIL-Rs in methods, or in the manufacture of a medicaments, for the treatment of the cancers described herein. Such methods may comprise administering to a subject in need of such treatment a therapeutically effective amount of an agent that decreases the biological activity. Agents capable of decreasing the biological activity may achieve their effect by a number of means. For instance, such an agent may be one which (by way of non-limiting example) decreases the expression of the TRAIL receptor; increases TRAIL receptor desensitisation or receptor breakdown; reduces interaction between TRAIL and its endogenous receptors; reduces TRAIL R mediated intracellular signalling; competes with endogenous TRAIL receptors for TRAIL binding; binds to the TRAIL receptors to block TRAIL binding; or binds to TRAIL preventing interaction with its receptors. It is preferred that the agent directly interacts with a receptor of TRAIL.

Thus in one preferred embodiment the compound binds to and blocks activity of TRAIL-R2 or its ligand TRAIL, or it binds and blocks the endogenous TRAIL-R2/TRAIL complex from forming properly so that it can no longer engage in the intracellular signalling that leads to Rac1 activation, enhanced migration and invasiveness.

In another embodiment, the compound is an antibody that binds to TRAIL and/or TRAIL-R2 blocking their activity. The antibodies in this invention may be monoclonal, polyclonal, chimeric, single chain antibodies or functional antibody fragments. Thus, this invention comprises any neutralising/blocking agent/inhibitor of TRAIL-R2 and/or TRAIL and their respective activities.

TRAIL inhibitors may optionally be selected from (without limitation) an antibody/functional antibody fragment or a soluble recombinant TRAIL-R (TRAIL-R1, TRAIL-R2, TRAIL-R3, TRAIL-R4 or OPG) molecule or a ligand-binding portion thereof or a TRAIL-R portion engineered to have increased ligand binding or a small molecule that may be identified to bind TRAIL and interfere with TRAIL-R binding.

Preferentially, TRAIL-R2-based fusion proteins as outlined in the Examples hereinafter e.g. Example 1 (FIG. 3), fragments thereof e.g. a TRAIL-R2-Fc fusion.

Preferred small molecules are those interfering with TRAIL-R2/TRAIL binding, since TRAIL-R2 has the highest affinity of the five TRAIL-Rs to TRAIL.

Some of these embodiments will now be described in more detail:

Cancers

By way of non-limiting example, the present invention may be applied to KRAS-mutated patients with pancreatic cancer, colon cancer, lung cancer, breast cancer, endometrial cancer, cervical cancer, liver cancer, myeloid leukemia, cholangiocarcinoma or bladder cancer. Other preferred cancers are described hereinafter. The most preferred target cancers are KRAS-mutated pancreatic, colon or lung cancers.

Antibodies

For the production of antibodies according to the invention, various host species may be immunised by injection with the above mentioned proteins to be targeted or any fragments of the two proteins which are immunogenic.

For example antibodies to neutralize TRAIL activity may be raised against full length human TRAIL, sequences are outlined in Example 5.

An appropriate adjuvant will be chosen depending on the host species in order to increase an immune response. Preferentially, peptides, fragments or oligopeptides used to induce an antibody response against them will contain at least five, but preferably ten amino acids. Monoclonal antibodies against the two proteins may be produced using any technique that provides for the production of antibody molecules or recombinant and non-recombinant functional fragments of these antibodies by continuous cell lines in culture. These include, but are not limited to, the hybridoma technique and the human B-cell hybridoma technique. In addition, techniques developed for the production of chimeric antibodies, e.g. recombinant antibodies can be used. Resulting antibodies may be used with or without modifications such as labelling, recombinant joining of antibody stretches or with molecules functioning as reporters. Modifications can be covalent and/or non-covalent.

Many different immune- and non-immunoassays may be used for screening to identify antibodies with the desired specificity. Various protocols for competitive binding and immunoradiometric assays using either polyclonal or monoclonal antibodies with already established specificity are well known in the field. These immunoassays typically involve measuring complex formation between TRAIL-R2 or TRAIL and their specific antibodies. A "Sandwich", i.e. two-sided, monoclonal-based immunoassay is preferred that comprises monoclonal antibodies against two non-interfering protein epitopes, but a competitive binding assay may also be used.

More specifically, it is preferred that the antibody is a γ-immunoglobulin (IgG).

It will be appreciated that the variable region of an antibody defines the specificity of the antibody and as such this region should be conserved in functional derivatives of the antibody according to the invention. The regions beyond the variable domains (C-domains) are relatively constant in sequence. It will be appreciated that the characterising feature of antibodies according to the invention is the $V_H$ and $V_L$ domains. It will be further appreciated that the precise nature of the $C_H$ and $C_L$ domains is not, on the whole, critical to the invention. In fact preferred antibodies according to the invention may have very different $C_H$ and $C_L$ domains. Furthermore preferred antibody functional derivatives may comprise the Variable domains without a C-domain (e.g. scFV antibodies).

An antibody derivative may have 75% sequence identity, more preferably 90% sequence identity and most preferably has at least 95% sequence identity to a monoclonal antibody or specific antibody in a polyclonal mix. It will be appreciated that most sequence variation may occur in the framework regions (FRs) whereas the sequence of the CDRs of the antibodies, and functional derivatives thereof, is most conserved.

A number of preferred embodiments of the invention relate to molecules with both Variable and Constant domains. However it will be appreciated that antibody fragments (e.g. scFV antibodies) are also encompassed by the invention that comprise essentially the Variable region of an antibody without any Constant region.

Antibodies generated in one species are known to have several serious drawbacks when used to treat a different species. For instance when murine antibodies are used in humans they tend to have a short circulating half-life in serum and are recognised as foreign proteins by the patient being treated. This leads to the development of an unwanted human anti-mouse (or rat) antibody response. This is particularly troublesome when frequent administrations of the antibody is required as it can enhance the clearance thereof, block its therapeutic effect, and induce hypersensitivity reactions. Accordingly preferred antibodies (if of non-human source) for use in human therapy are humanised.

Monoclonal antibodies are generated by the hybridoma technique which usually involves the generation of non-human mAbs. The technique enables rodent monoclonal antibodies with almost any specificity to be produced. Accordingly preferred embodiments of the invention may use such a technique to develop monoclonal antibodies against the TRAIL receptors. Although such antibodies are useful therapeutically, it will be appreciated that such antibodies are not ideal therapeutic agents in humans (as suggested above). Ideally, human monoclonal antibodies would be the preferred choice for therapeutic applications. However, the generation of human mAbs using conventional cell fusion techniques has not to date been very successful. The problem of humanisation may be at least partly addressed by engineering antibodies that use V region sequences from non-human (e.g. rodent) mAbs and C region (and ideally FRs from V region) sequences from human antibodies. The resulting 'engineered' mAbs are less immunogenic in humans than the rodent mAbs from which they were derived and so are better suited for clinical use.

Humanised antibodies may be chimaeric monoclonal antibodies, in which, using recombinant DNA technology, rodent immunoglobulin constant regions are replaced by the constant regions of human antibodies. The chimaeric H chain and L chain genes may then be cloned into expression vectors containing suitable regulatory elements and induced into mammalian cells in order to produce fully glycosylated antibodies. By choosing an appropriate human H chain C region gene for this process, the biological activity of the antibody may be pre-determined. Such chimaeric antibodies are superior to non-human monoclonal antibodies in that their ability to activate effector functions can be tailored for a specific therapeutic application, and the anti-globulin response they induce is reduced.

Such chimaeric molecules are preferred agents for treating cancer according to the present invention. RT-PCR may be used to isolate the $V_H$ and $V_L$ genes from preferred mAbs, cloned and used to construct a chimaeric version of the mAb possessing human domains.

Further humanisation of antibodies may involve CDR-grafting or reshaping of antibodies. Such antibodies are produced by transplanting the heavy and light chain CDRs of a rodent mAb (which form the antibody's antigen binding site) into the corresponding framework regions of a human antibody.

Commercially available monoclonal TRAIL-neutralizing antibodies are, for example anti-human TRAIL clone 2E5 from Enzo (www.enzolifesciences.com/ALX-804-296/trail-human-mab-2e5/) and Anti-TRAIL antibody [75411.11] (ab10516) from Abcam (www.abcam.com/TRAIL-antibody-75411-11-ab10516.html).

Fragments or Fusion Proteins

Agents as described herein may be based on portions (e.g. soluble fragments) of TRAIL receptors, optionally fused to heterologous protein domains or combined with non-protein moieties.

In one embodiment a TRAIL inhibitor comprises the extracellular domain of TRAIL-R1, TRAIL-R2, TRAIL-R3, TRAIL-R4 or OPG, preferentially that of TRAIL-R2, or a ligand-binding portion thereof, or the extracellular domain of the mature TRAIL-R2 sequence according to Walczak et al. (Walczak et al., 1997) and a patent by C. T. Rauch and H. Walczak (U.S. Pat. No. 6,569,642 B1), which is incorporated herein by reference, which may be fused to a heterologous polypeptide domain, particularly an Fc portion of an immunoglobulin molecule, including or not the hinge region or part thereof, e.g. from a human IgG molecule, preferably an Fc region of human IgG1, IgG2, IgG3 or human IgG4 with or without the hinge region or a part thereof.

The way the two fully human protein parts are fused can be done in a manner that reduces the immunogenicity potential of the resulting fusion protein as described in Walczak (WO/2004/085478; PCT/EP2004/003239: "Improved Fc fusion proteins").

Because there are two splice forms of TRAIL-R2 expressed and the splicing affects the extracellular domain of TRAIL-R2 (Screaton et al., 1997) at least two extracellular domains of TRAIL-R2 with differing amino acid sequences are known. In one embodiment, the TRAIL-binding portion of the extracellular domain of TRAIL-R2 can come from either one of these two when constructing TRAIL-inhibiting TRAIL-R2 fusion proteins.

TRAIL-R fusion proteins that bind to and neutralize TRAIL activity may be produced using any technique that provides for the production of recombinant and non-recombinant full length or functional fragments of these proteins by continuous cell lines in culture. These include, but are not limited to, the production of recombinant proteins by HEK293T cells as outlined in Example 2.

As described below, resulting proteins may be used with or without modifications such as labelling, recombinant joining of antibody stretches or with molecules functioning as reporters. Modifications can be covalent and/or non-covalent.

Peptide Agents

It will be appreciated that peptide or protein agents used or provided according to the invention may be derivatives of native or original sequences, and thus include derivatives that increase the effectiveness or half-life of the agent in vivo. Examples of derivatives capable of increasing the half-life of polypeptides according to the invention include peptoid derivatives, D-amino acid derivatives and peptide-peptoid hybrids.

Proteins and peptide agents according to the present invention may be subject to degradation by a number of means (such as protease activity at a target site). Such degradation may limit their bioavailability and hence therapeutic utility. There are a number of well-established techniques by which peptide derivatives that have enhanced stability in biological contexts can be designed and produced. Such peptide derivatives may have improved bioavailability as a result of increased resistance to protease-mediated degradation. Preferably, a derivative suitable for use according to the invention is more protease-resistant than the protein or peptide from which it is derived. Protease-resistance of a peptide derivative and the protein or peptide from which it is derived may be evaluated by means of well-known protein degradation assays. The relative values of protease resistance for the peptide derivative and peptide may then be compared. Peptoid derivatives of proteins and peptides according to the invention may be readily designed from knowledge of the structure of the receptor according to the first aspect of the invention or an agent according to the fourth, fifth or sixth aspect of the invention. Commercially available software may be used to develop peptoid derivatives according to well-established protocols.

Retropeptoids, (in which all amino acids are replaced by peptoid residues in reversed order) are also able to mimic proteins or peptides according to the invention. A retropeptoid is expected to bind in the opposite direction in the ligand-binding groove, as compared to a peptide or peptoid-peptide hybrid containing one peptoid residue. As a result, the side chains of the peptoid residues are able to point in the same direction as the side chains in the original peptide.

A further embodiment of a modified form of peptides or proteins according to the invention comprises D-amino acid forms. In this case, the order of the amino acid residues is reversed. The preparation of peptides using D-amino acids rather than L-amino acids greatly decreases any unwanted breakdown of such derivative by normal metabolic processes, decreasing the amounts of the derivative which needs to be administered, along with the frequency of its administration.

Nucleic Acids

In a further embodiment of the present invention the inhibitor is a nucleic acid effector molecule.

The nucleic acid effector molecule may be DNA, RNA (including siRNA, miRNA and shRNA), PNA or a DNA-RNA-hybrid molecule. These may be specifically directed towards down-regulation of TRAIL or TRAIL-R sequences (see e.g. Example 5). siRNA forms part of a gene silencing mechanism, known as RNA interference (RNAi) which results in the sequence-specific destruction of mRNAs and enables a targeted knockout of gene expression. siRNA used in gene silencing may comprise double stranded RNA of 21 nucleotides length, typically with a 2-nucleotide overhang at each 3' end. Alternatively, short hairpin RNAs (shRNAs) using sense and antisense sequences connected by a hairpin loop may be used. Both siRNAs and shRNAs can be either chemically synthesized and introduced into cells for transient RNAi or expressed endogenously from a promoter for long-term inhibition of gene expression. siRNA molecules for use as an agent according to the invention may comprise either double stranded RNA of 10-50 nucleotides. Preferably, siRNAs for use as an agent according to the invention comprise 18-30 nucleotides. More preferably, siRNAs for use as an agent according to the invention comprise 21-25 nucleotides. And most preferably, siRNAs for use as an agent according to the invention comprise 21 nucleotides. It will be appreciated that siRNAs will need to be based upon the sequences according to the second aspect of the invention. Preferred double stranded siRNA molecules comprise a sense strand of 21-25 contiguous nucleotides from a sequence of the TRAIL or its receptors bound to the complementary antisense strand. Alternatively, shRNAs using sense and antisense sequences may be used as an agent according to the invention. Preferably, shRNAs using sense and antisense sequences that may be employed as an agent according to the invention comprise 20-100 nucleotides.

In other embodiments the nucleic acid may encode other agents of the invention—for example the fusion proteins described herein based on Trail or Trail Rs It may be single or double-stranded. The nucleic acid effector molecule may be delivered directly as a drug (this could be "naked" or e.g. in liposomes) it may be expressed from a retrovirus, adenovirus, herpes or vaccinia virus or bacterial plasmids for delivery of nucleotide sequences to the targeted organ, tissue or cell population.

These constructs may be used to introduce untranslatable sense or antisense sequences into a cell.

Without integration into the DNA, these vectors may continue to produce RNA molecules until degradation by cellular nucleases. Vector systems may result in transient expression for one month or more with a non-replicating vector and longer if appropriate replication elements are part of the vector system.

Thus, as is well known in the art, recombinant vectors may include other functional elements. For instance, recombinant vectors can be designed such that the vector will autonomously replicate in the cell. In this case, elements which induce DNA replication may be required in the recombinant vector. Alternatively, the recombinant vector may be designed such that the vector and nucleic acid molecule integrates into the genome of a cell. In this case DNA sequences which favour targeted integration (e.g. by homologous recombination) are desirable. Recombinant vectors may also have DNA coding for genes that may be used as selectable markers in the cloning process. The recombinant vector may also further comprise a promoter or regulator to control expression of the nucleic acid as required.

Variants

Wherever amino acid and nucleic acid sequences are discussed herein (for example in respect of coding fusion proteins or other agents), it will be appreciated by the skilled technician that functional derivatives of the amino acid, and nucleic acid sequences, disclosed herein, are also envisaged—such derivatives may have a sequence which has at least 30%, preferably 40%, more preferably 50%, and even more preferably, 60% sequence identity with the amino acid/polypeptide/nucleic acid sequences of any of the sequences referred to herein. An amino acid/polypeptide/nucleic acid sequence with a greater identity than preferably 65%, more preferably 75%, even more preferably 85%, and even more preferably 90% to any of the sequences referred to is also envisaged. Preferably, the amino acid/polypeptide/nucleic acid sequence has 92% identity, even more preferably 95% identity, even more preferably 97% identity, even more preferably 98% identity and, most preferably, 99% identity with any of the referred to sequences.

Calculation of percentage identities between different amino acid/polypeptide/nucleic acid sequences may be carried out as follows. A multiple alignment is first generated by the ClustalX program (pair wise parameters: gap opening 10.0, gap extension 0.1, protein matrix Gonnet 250, DNA matrix IUB; multiple parameters: gap opening 10.0, gap extension 0.2, delay divergent sequences 30%, DNA transition weight 0.5, negative matrix off, protein matrix gonnet series, DNA weight IUB; Protein gap parameters, residue-specific penalties on, hydrophilic penalties on, hydrophilic residues GPSNDQERK, gap separation distance 4, end gap separation off). The percentage identity is then calculated from the multiple alignment as (N/T)*100, where N is the number of positions at which the two sequences share an identical residue, and T is the total number of positions compared. Alternatively, percentage identity can be calculated as (N/S)*100 where S is the length of the shorter sequence being compared. The amino acid/polypeptide/nucleic acid sequences may be synthesised de novo, or may be native amino acid/polypeptide/nucleic acid sequence, or a derivative thereof.

Alternatively, a substantially similar nucleotide sequence will be encoded by a sequence which hybridizes to any of the nucleic acid sequences referred to herein or their complements under stringent conditions. By stringent conditions, we mean the nucleotide hybridises to filter-bound DNA or RNA in 6× sodium chloride/sodium citrate (SSC) at approximately 45° C. followed by at least one wash in 0.2×SSC/0.1% SDS at approximately 5-65° C. Alternatively, a substantially similar polypeptide may differ by at least 1, but less than 5, 10, 20, 50 or 100 amino acids from the peptide sequences according to the present invention.

Due to the degeneracy of the genetic code, it is clear that any nucleic acid sequence could be varied or changed without substantially affecting the sequence of the receptor protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid.

The accurate alignment of protein or DNA has been investigated in detail by a number of researchers. Of particular importance is the trade-off between optimal matching of sequences and the introduction of gaps to obtain such a match. In the case of proteins, the means by which matches are scored is also of significance. The family of PAM matrices (e.g., Dayhoff, M. et al., 1978, Atlas of protein sequence and structure, Natl. Biomed. Res. Found.) and BLOSUM matrices quantify the nature and likelihood of conservative substitutions and are used in multiple alignment algorithms, although other, equally applicable matrices will be known to those skilled in the art. The popular multiple alignment program ClustalW, and its windows version ClustalX (Thompson et al., 1994, Nucleic Acids Research, 22, 4673-4680; Thompson et al., 1997, Nucleic Acids Research, 24, 4876-4882) are efficient ways to generate multiple alignments of proteins and DNA.

Frequently, automatically generated alignments require manual alignment, exploiting the trained user's knowledge of the protein family being studied, e.g., biological knowledge of key conserved sites. One such alignment editor programs is Align (www.gwdg.de/~dhepper/download/; Hepperle, D., 2001: Multicolor Sequence Alignment Editor. Institute of Freshwater Ecology and Inland Fisheries, 16775 Stechlin, Germany), although others, such as JalView or Cinema are also suitable.

Calculation of percentage identities between proteins occurs during the generation of multiple alignments by Clustal. However, these values need to be recalculated if the alignment has been manually improved, or for the deliberate comparison of two sequences. Programs that calculate this value for pairs of protein sequences within an alignment include PROTDIST within the PHYLIP phylogeny package (Felsenstein; evolution.gs.washington.edu/phylip.html) using the "Similarity Table" option as the model for amino acid substitution (P). For DNA/RNA, an identical option exists within the DNADIST program of PHYLIP.

Other modifications in protein sequences are also envisaged and within the scope of the claimed invention, i.e. those which occur during or after translation, e.g. by acetylation, amidation, carboxylation, phosphorylation, proteolytic cleavage or linkage to a ligand.

Compositions

The present invention also provides a pharmaceutical composition, comprising at least one agent that binds TRAIL or TRAIL-R2 or that neutralises the pro-tumourigenic signalling of TRAIL/TRAIL-R2 (which relies on Rac1 activity). The present invention also provides a method for treating patients with KRAS-mutated cancer or cancers that are wild type in KRAS but have developed other means to result in ROCK inhibition as outlined in example 1 (FIG. 7) and published for integrin signalling through Src and FAK (Ahn et al., 2010), BRAF (Klein et al., 2008), Raf-1 (Ehrenreiter et al., 2009) and Notch3 (Belin de Chantemele et al., 2008), by administering one of the pharmaceutical compositions contemplated herein.

In another preferred embodiment the pharmaceutical composition may comprise further active agents for the treatment of cancer and in particular KRAS-mutated cancers including pancreatic, colon or lung cancer but also KRAS-mutated cancers that occur in other tissues, including haematological malignancies.

The pharmaceutical compositions may be administered alone or in combination with at least one other agent, such as stabilising compounds, which may be administered in any sterile, biocompatible pharmaceutical carrier solution, including, but not limited to saline, buffered saline, dextrose and water. The compositions may be administered to patients alone or in combination with other agents, drugs or hormones. The pharmaceutical compositions detailed in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual or rectal means.

Dosages and Regimens

Pharmaceutical compositions suitable for use in the invention include compositions wherein the active ingredients are contained in an effective amount to achieve the intended purpose. The determination of an effective dose is well within the capability trained personnel. For any compounds, the therapeutically effective dose can be estimated initially either in cell culture assays, e.g., of cell lines or in animal models, usually but not exclusively mice. The animal model may also be used to determine the appropriate concentration range and route of administration. Based on such pilot experiments, useful doses and routes for administration in humans can be determined. A therapeutically effective dose refers to that amount of active ingredient, for example a nucleic acid or a protein of the invention or an antibody, which is sufficient for treating a specific condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as LD50/ED50. Pharmaceutical compositions, which exhibit large therapeutic indices, are preferred. The dosage is preferably within a range of circulating concentrations that include the ED50 with little or no toxicity. The dosage varies within this range depending upon the dosage employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state (stage of the cancer), general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week or once every two weeks depending on half-life and clearance rate of the particular formulation. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art employ different formulations for nucleotides than for proteins or their inhibitors. Similarly, delivery of polynucleotides or polypeptides will be specific to particular cells and conditions as detailed above.

In another embodiment, the preferred dosage of an agent (e.g. a TRAIL-R2-Fc fusion protein) may be 20-500 mg twice per week, weekly, every ten days, bi-weekly, every three weeks, or every four weeks.

Most preferably the given dose will be between 50 mg and 200 mg twice per week, weekly, or bi-weekly.

In another embodiment of this invention these dosages may be used for a TRAIL-binding and -neutralizing antibody or other fusion proteins containing the extracellular domains of other TRAIL-Rs, namely TRAIL-R1, -R3, -R4 or OPG.

Combination Therapies

In some embodiments the methods or treatments of the present invention may be combined with other therapies, whether symptomatic or disease modifying e.g. a second therapeutic agent believed to show therapeutic benefit in the relevant cancers.

The term "treatment" includes combination treatments and therapies, in which two or more treatments or therapies are combined, for example, sequentially or simultaneously.

For example it may be beneficial to combine treatment with an agent or compound as described herein with one or more other (e.g., 1, 2, 3, 4) agents or therapies.

Appropriate examples of co-therapeutics will be known to those skilled in the art on the basis of the disclosure herein. Typically the co-therapeutic may be any known in the art which it is believed may give therapeutic effect in treating the cancers described herein e.g. KRAS oncogenic related cancers.

Thus in one embodiment of this invention, the agent or invention is applied to an individual with a cancer (e.g. pancreatic cancer, colon cancer, lung cancer, breast cancer, endometrial cancer, cervical cancer, liver cancer, myeloid leukemia, cholangiocarcinoma or bladder cancer) in combination with a standard chemo-/and/or radiotherapy that is given in the respective cancer [e.g. cisplatin, Carboplatin, etoposide, gemcitabine, Vinorelbine, Paclitaxel (Taxol), Docetaxel (Taxotere), Doxorubicin, Pemetrexed, Fluorouracil (also called 5FU), Capecitabine, Oxaliplatin, Irinotecan (Camptothecin), Uftoral (also called tegafur with uracil), folinic acid, Cyclophosphamide, Epirubicin. Methotrexate, Mitomycin, Mitozantrone, or any combination thereof]

Thus in one embodiment of this invention, the agent or invention is applied to an individual with a cancer which is KRAS-mutated, and the standard chemo-/and/or radiotherapy is e.g. cisplatin, Carboplatin, etoposide, gemcitabine, Vinorelbine, Paclitaxel (Taxol), Docetaxel (Taxotere), Doxorubicin, Pemetrexed, Fluorouracil (also called 5FU), Capecitabine, Oxaliplatin, Irinotecan (Camptothecin), Uftoral (also called tegafur with uracil), folinic acid, Cyclophosphamide, Epirubicin. Methotrexate, Mitomycin, Mitozantrone, or any combination thereof.

Preferably the cancer is KRAS-mutated pancreatic, colon and lung cancers and the standard chemo-/and/or radiotherapy is e.g. cisplatin, Carboplatin, etoposide, gemcitabine, Vinorelbine, Paclitaxel (Taxol), Docetaxel (Taxotere), Doxorubicin, Pemetrexed, Fluorouracil (also called 5FU), Capecitabine, Oxaliplatin, Irinotecan (Camptothecin), Uftoral (also called tegafur with uracil), folinic acid, or any combination thereof.

The particular combination would be at the discretion of the physician who would also select dosages using his/her common general knowledge and dosing regimens known to a skilled practitioner.

The agents (i.e., a compound as described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., a compound as described here, plus one or more other agents) may be formulated together in a single dosage form, or alternatively, the individual agents may be formulated separately and presented together in the form of a kit, optionally with instructions for their use.

Detection of KRAS Mutations and Kits

The invention may comprise screening patients for the KRAS or other mutation (e.g. by PCR of a sample from the individual) in order to select or reject them for treatment with the agents described herein ("companion diagnostics").

A commercially available diagnostic kit for detecting mutations in the KRAS oncogene is, for example, the TheraScreen™ K-Ras mutation detection kit, for detecting the mutations 12Ala, 12Asp, 12Arg, 12Cys, 12Ser, 12Val and 13Asp.

A diagnostic kit for detecting mutations in the KRAS oncogene is, for example, the TheraScreen™ KRAS PCR kit by Qiagen.

Another, and preferred commercially available diagnostic kit herein for identifying mutations in the KRAS gene is the Cobas™ KRAS Mutation Test by Roche (molecular.roche.com/assays/Pages/cobasKRASMutationTest.aspx), which is a real-time PCR test that can be used for detecting a broad spectrum of mutations in codons 12, 13 and 61 of the KRAS gene, covering the mutations 12D, 12V, 12C, 12A, 12S, 12R, 12F, 13D, 13C, 13R, 13S, 13A, 13V, 131, 61H, 61L, 61R, 61K, 61E and 61P. This kit was observed to yield best results in formalin fixed tissues (Gonzalez de Castro et al., 2012).

For mutational testing a typical cancer (tumour) sample comprising nucleic acid is used, which may be selected from the group consisting of a tissue, a biopsy probe, cell lysate, cell culture, cell line, organ, organelle, biological fluid, blood sample, urine sample, skin sample, and the like.

The present invention further provides the use of such KRAS mutation kits as companion diagnostic to this invention i.e. neutralization of TRAIL and/or TRAIL-R2 activity reducing cancer cell transformation, migration and metastasis in KRAS-mutated cancer patients.

The present invention further includes the use of such kits for determining likelihood of effectiveness of treatment by TRAIL- and/or TRAIL-R2-blocking agents, optionally in combination with one or more other anti-cancer agents, in a mammalian, preferably human, patient diagnosed with cancer (such as KRAS-mutated cancers described herein), said kit preferably comprising means for detecting one or more mutations in the KRAS oncogene described herein.

Screening System

Another aspect of the present invention relates to a method for screening for an agent, which modulates/affects, and preferably neutralises, the activity of TRAIL or TRAIL-R2, or an agent for use in a therapy described herein, which method comprises the steps:

(a) incubating a mixture comprising
  (i) TRAIL-R2 and/or TRAIL or functional fragments thereof
  (ii) a candidate agent
under conditions whereby TRAIL or TRAIL-R2 or a functional fragment thereof has a reference biological activity;
(b) detecting the biological activity of TRAIL or TRAIL-R2 or functional fragments thereof to determine an activity in the presence of the agent;
(c) determining a difference between the biological activity in the presence of the agent and the reference biological activity.

Thus in one aspect of the present invention there is provided a method of screening a compound to test whether or not the compound has efficacy for treating a cancer described herein, comprising:

(i) exposing cells or membranes comprising a TRAIL receptor to a test compound for a predetermined length of time;
(ii) detecting the biological activity or expression of the TRAIL receptor; and
(iii) comparing the activity or expression of the TRAIL receptors in the cells or membranes treated with the compound relative to activity or expression found in control cells or membranes that were not treated with the compound
wherein compounds with efficacy for treating cancers as described herein decrease activity or decrease expression of the TRAIL receptor relative to the controls.

The biological activity in this aspect may be TRAIL to receptor binding; detection of receptor-mediated intracellular signal transduction; or determination of an end-point physiological effect. By "expression" we mean detection of the receptor protein either in the cell membrane, the Endoplasmatic Reticulum or the Golgi Apparatus; or detection of the mRNA encoding the receptor protein.

According to a preferred embodiment of such an assay, an agent to be screened for prevents or reduces Rac1 activation by TRAIL-R2 or TRAIL.

Another preferred embodiment of such an assay is an agent that disrupts, prevents or reduces the interaction between TRAIL and TRAIL-R2 or fragments thereof, as described hereinabove and below.

Agents (or candidate therapeutic molecules) of the present invention may include, by way of non-limiting example, peptides produced by expression of an appropriate nucleic acid sequence in a host cell or using synthetic organic chemistries, or non-peptide small molecules produced using conventional synthetic organic chemistries well known in the art. Screening assays may be automated in order to facilitate the screening of a large number of small molecules at the same time.

As used herein, the terms "candidate therapeutic compound" refers to a substance that is believed to interact with one of the target proteins of the invention (or a fragment thereof), and which can be subsequently evaluated for such an interaction.

Representative candidate therapeutic compounds include "xenobiotics", such as drugs and other therapeutic agents, natural products and extracts, carcinogens and environmental pollutants, as well as "endobiotics" such as steroids, fatty acids and prostaglandins. Other examples of candidate compounds that can be investigated using the methods of the present invention include, but are not restricted to toxins and venoms, viral epitopes, hormones (e. g., opioid peptides, steroids, etc.), hormone receptors, peptides, enzymes, enzyme substrates, co-factors, lectins, sugars, oligonucleotides or nucleic acids, oligosaccharides, proteins, small molecules and monoclonal antibodies.

Screening methods may be cell-based or cell-free.

In one preferred embodiment the present invention provides a method of drug screening utilising eukaryotic or prokaryotic host cells stably transformed with recombinant polynucleotides expressing the target protein of the invention or a fragment thereof, preferably in competitive binding assays. Such cells, either in viable or fixed form, can be used for standard binding assays. For example, the assay may measure the formation of complexes between a target protein and the agent being tested, or examine the degree to which the formation of a complex between the target protein or fragment thereof and a known ligand or binding partner is interfered with by the agent being tested. Thus, the present invention provides methods of screening for drugs comprising contacting such an agent with the target protein of the invention or a fragment thereof or a variant thereof found in a tumour cell and assaying (i) for the presence of a complex between the agent and the target protein, fragment or variant thereof, or (ii) for the presence of a complex between the target protein, fragment or variant and a ligand or binding partner. In such competitive binding assays the target protein or fragment or variant is typically labelled. Free target protein, fragment or variant thereof is separated from that present in a protein: protein complex and the amount of free (i.e. uncomplexed) label is a measure of the binding of the agent being tested to the target protein or its interference with binding of the target protein to a ligand or binding partner, respectively.

Alternatively, an assay of the invention may measure the influence of the agent being tested on a biological activity of the target protein. Thus, the present invention provides methods of screening for drugs comprising contacting such an agent with the target protein of the invention or a fragment thereof or a variant thereof found in a tumour cell and assaying for the influence of such an agent on a biological activity of the target protein, by methods well known in the art. In such activity assays the biological activity of the target protein, fragment or variant thereof is typically monitored by provision of a reporter system. For example, this may involve provision of a natural or synthetic substrate that generates a detectable signal in proportion to the degree to which it is acted upon by the biological activity of the target molecule.

It is contemplated that, once candidate therapeutic compounds have been elucidated, rational drug design methodologies well known in the art may be employed to enhance their efficacy. The goal of rational drug design is to produce structural analogues of biologically active polypeptides of interest or of small molecules with which they interact (e.g. agonists, antagonists, inhibitors) in order to fashion drugs which are, for example, more active or stable forms of the polypeptide, or which, for example, enhance or interfere with the function of a polypeptide in vivo. In one approach, one first determines the three-dimensional structure of a protein of interest, such as the target protein of the invention or, for example, of the target protein in complex with a ligand, by x-ray crystallography, by computer modelling or most typically, by a combination of approaches. For example, the skilled artisan may use a variety of computer programmes which assist in the development of quantitative structure activity relationships (QSAR) that act as a guide in the design of novel, improved candidate therapeutic molecules. Less often, useful information regarding the structure of a polypeptide may be gained by modelling based on the structure of homologous proteins. In addition, peptides can be analysed by alanine scanning (Wells, Methods Enzymol. 202: 390-411, 1991), in which each amino acid residue of the peptide is sequentially replaced by an alanine residue, and its effect on the peptide's activity is determined in order to determine the important regions of the peptide. It is also possible to design drugs based on a pharmacophore derived from the crystal structure of a target-specific antibody selected by a functional assay. It is further possible to avoid the use of protein crystallography by generating anti-idiotypic antibodies to such a functional, target-specific antibody, which have the same three-dimensional conformation as the original target protein. These anti-idiotypic antibodies can subsequently be used to identify and isolate peptides from libraries, which themselves act as pharmacophores for further use in rational drug design.

For use as a medicament in vivo, candidate therapeutic compounds so identified may be combined with a suitable pharmaceutically acceptable carrier, such as physiological saline or one of the many other useful carriers well characterized in the medical art, and formulated as compositions as described above.

Wherever a method of treatment employing an agent is described herein, it will be appreciated that an agent for use in that method is also described, as is an agent for use in the manufacture of a medicament for treating the relevant cancers. Wherever a composition is described herein, it will be appreciated that the same composition for use in the therapeutic methods (including prophylactic methods) described herein is also envisaged, as is the composition for use in the manufacture of a medicament for treating the relevant cancers.

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Any sub-titles herein are included for convenience only, and are not to be construed as limiting the disclosure in any way.

The invention will now be further described with reference to the following non-limiting Figures and Examples.

Other embodiments of the invention will occur to those skilled in the art in the light of these.

BRIEF DESCRIPTION OF THE FIGURES

FIGS. 1A-1H| KRAS-mediated transformation depends on autocrine TRAIL/TRAIL-R2 stimulation. FIG. 1A, A549, DLD-1, PancTu I and Colo357 were transfected with the indicated siRNAs and subjected to migration assays using the xCELLigence system. FIG. 1B, Six KRAS-mutated and five KRAS-WT cell lines were transfected with the indicated siRNAs and subjected to migration assays. FIG. 1C, Five KRAS-mutated and KRAS-WT cell lines were transfected with siRNAs silencing KRAS and subjected to migration assays. FIG. 1D, Isogenic KRAS-mutated (DLD-1) and KRAS-WT (DKO4) cells were transfected as indicated and subjected to migration assays. Migration was normalized to control transfected DKO4 cells. FIG. 1E, A549 cells were subjected to the indicated knockdowns and migration assays. FIG. 1F, A549 cells were incubated in presence or absence of 100 μg/ml of the indicated recombinant receptor-Fc protein during migration experiments as before. Migration was normalized to PBS-treated cells. FIG. 1G, A549 cells stably transfected with vector, control shRNA, shRNA against TRAIL-R1 and TRAIL-R2 were subjected to colony formation assays in soft agar. Relative colony formation was determined normalized to vector-infected cells after 4 weeks. FIG. 1H, Representative images of unstained colonies grown in soft agar (200×).

Figure 7A:
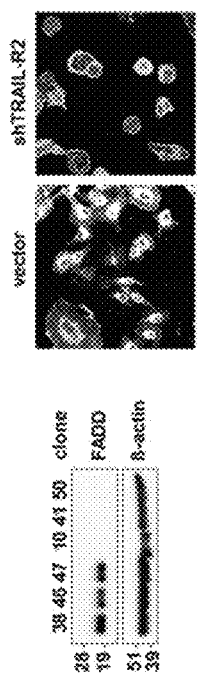

All figures represent means of three independent experiments +/−SEM, individual dots represent means of three experiments of one cell line. Ctr, Control; TR1, TRAIL-R1; TR2, TRAIL-R2; mut, mutated; WT, wild type; ns, not significant; * P<0.05,  P<0.01 and * p<0.0001 Student's t-test (FIGS. 1B and 1C) or ANOVA.

FIGS. 2A-2F| TRAIL-R2, but not TRAIL-R1, is required for migration of KRAS—but not HRAS-mutated cancer cells. FIG. 2A, Cell lines were stained for surface expression of TRAIL-R1 to TRAIL-R4. FIG. 2B, Cells were subjected to the indicated knockdowns for 24 h and proliferation was determined by BrdU-incorporation after another 24 h incubation. FIG. 2C, A549 cells were subjected to transient knockdown of TRAIL-R2 using individual siRNA sequences (#1-4) or a pool consisting of these four sequences and subjected to migration assays using the xCELLigence system. FIG. 2D, A549 cells infected with empty vector or shRNAs targeting TRAIL-R1 or TRAIL-R2 were subjected to xCELLigence migration assays. FIG. 2E, DT8082 cells (murine) were subjected to the indicated knockdowns followed by migration assays as before. FIG. 2F, DT02 cells (murine) were subjected to migration as in FIG. 2E. Representative Western Blots are shown.

All values represent mean+/−SEM of three independent experiments or one representative experiment out of three (FIG. 2A). Ctr, Control; ns, not significant; * P<0.05;  P<0.01 and * p<0.0001 Student's t-test (FIG. 2E and FIG. 2F) or ANOVA.

FIGS. 3A-3D| KRAS-mutated cells require autocrine TRAIL-R2-mediated migration for metastasis formation. FIG. 3A, 2×106 A549-luc cells infected with shTRAIL-R2 or control vector were injected into the tail vein of SCID beige mice. Metastatic burden in the lungs was detected after three weeks by quantification of bioluminescence (Photons/second). Three representative mice from each group are shown (n=9/group). FIG. 3B, FIG. 3C Five lungs from each group that were closest to the average value of the respective group in the H&E quantification were subjected to further Ki67 and TUNEL stainings and quantified as Ki67 and TUNEL positive area within tumor nodules, respectively. Representative images are shown. FIG. 3D, A549-luc parental cells were injected as in FIG. 3A, mice were treated with Vehicle (PBS) or 0.5 mg TRAIL-R2-Fc/mouse starting the next day, 3× per week.

Bioluminescence was determined after 2 weeks, representative mice are shown (n=8/group). Arrows indicate Ki67/TUNEL-positive cells. Dots represent individual lungs. Values are means+/−SEM; ns, not significant; * P<0.05 Student's t-test.

FIGS. 4A-4G| Endogenous TRAIL-R2 is required for experimental lung metastasis. FIG. 4A, H&E-stained paraffin sections of lungs from all mice were subjected to microscopical analysis estimating the percentage of total lung area occupied by tumor tissue. Representative images are shown. Arrows indicate metastatic foci. FIG. 4B, After the experimental endpoint was reached, lungs were removed. Photos of all lungs are shown. FIG. 4C, The indicated shRNA-infected A549-luc cells were seeded at the indicated cell numbers and subjected to in vitro luciferase activity assays. FIG. 4D, 2×106 of the indicated shRNA-infected A549-luc cells were injected into the tail vein of SCID beige mice. Metastatic burden in the lungs was detected by quantification of bioluminescence (photons/second) after 1 week using the IvisSpectrum Imaging system. Images of three representative mice from each group are shown. FIG. 4E, 1.5×10$^6$ A549-luc cells stably infected with shTRAIL-R2 or control vector were injected subcutaneously into both flanks of SCID beige mice (n=10 tumours/group). Tumor volumes were measured with a caliper after three weeks. FIG. 4F, Subcutaneous tumours of both groups are shown. FIG. 4G, Treatment schedule for lung metastasis bearing (A549) SCID beige mice.

Data represent mean+/−SEM of three independent experiments. Dots represent individual mice/lungs/tumours of mice (n=9/group)+/−SEM. ns, not significant; * P<0.05 (Student's t-test).

FIGS. 5A-5E| KRAS-driven PanIN formation and spontaneous metastasis of PDAC genetically depend on mTRAIL-R. FIG. 5A, Pancreata of 4.5 months-old KC-mice were removed, fixed, stained with H&E and the number of PanINs per pancreatic section was determined by histopathological examination (KC-mTRAIL-Rwt/wt (black box) n=8 and KC-mTRAIL-Rfl/fl (white box) n=7). FIG. 5B, Representative H&E, αCK19 and DAPI stainings showing PanINs (200×). FIG. 5C, Survival (Kaplan-Meier) of KPC-TRAIL-Rwt/wt (solid circles) and KPC-TRAIL-Rfl/fl mice (open circles). FIG. 5D, Animals with metastasis at time of death were quantified. FIG. 5E, Representative H&E stainings of pancreatic adenocarcinomas and lung tissues are shown (100×), Met=Metastasis.

Values are means+/−SEM * P<0.05 Student's t-test (FIG. 5A); Kaplan-Meier statistics were determined by log-rank test p=0.0096 (FIG. 5C), Fisher's exact test (FIG. 5D, mice with metastasis, p=0.0476).

FIGS. 6A-6C| Validation of the KPC-mouse model in the presence or absence of mTRAIL-R. FIG. 6A, Genotyping PCR and a PCR detecting a recombination product were performed on both, a representative KPC-TRAIL-Rwt/wt and a KPC-TRAIL-Rfl/fl mouse; T=Tail; E=Ear; P=Pancreas. FIG. 6B, A representative KPC mouse with ascites accumulation and a large pancreatic tumour is shown. FIG. 6C, Size of solid pancreatic tumours was determined at time of death (TOD) using a caliper (KPC-TRAIL-Rwt/wt (black bar) n=6; KPC-TRAIL-Rfl/fl (white bar) n=5).

Data represent mean+/−SEM. Fl, Floxed allele; Wt, wild type allele; Rec, recombined allele; ns, not significant; (Student's t-test).

Figure 7B:
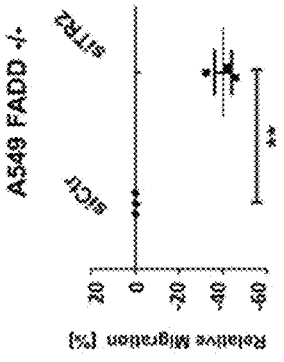
Figure 7C:
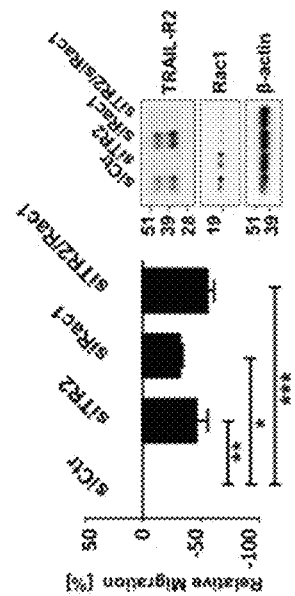
Figure 7D:
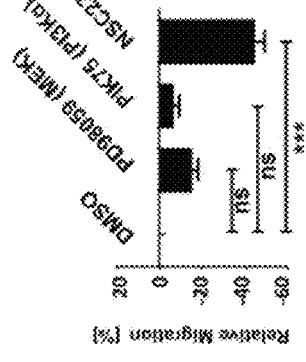
Figure 7E:
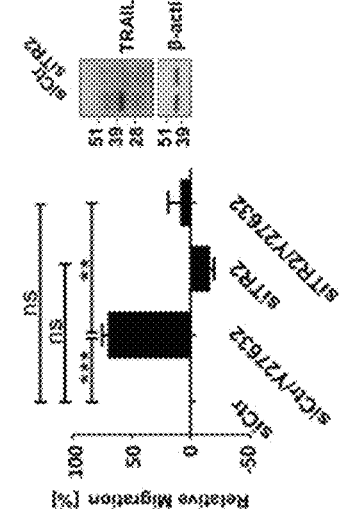
Figure 7F:

FIGS. 7A-7F| Autocrine migration is independent of the DISC but requires Rac1. FIG. 7A, FADD-deficient clones 10, 41 and 50 were transfected with the indicated siRNAs and subjected to migration assays. FIG. 7B, Control vector-infected or shTRAIL-R2-infected A549 cells were fixed and stained using Texas red-coupled phalloidin and DAPI. Representative confocal images are shown (×400).c, A549 cells were treated with DMSO, PD98059 (10 µM), PIK75 (100 nM) or NSC23766 (100 µM) and subjected to migration assays. FIG. 7D, A549 cells were transfected with the indicated siRNAs and subjected to migration assays. FIG. 7E, Isogenic DLD-1 and DKO4 cells were treated with iz-TRAIL (100 ng/ml) for the indicated times and then subjected to pulldown of GTP-bound Rac1 using PAK1-beads (Millipore-Rac1 activation kit). FIG. 7F, KRAS-WT DKO4 cells were transfected with the indicated siRNAs and prior to migration treated with vehicle ($H_2O$) or 10 µM Y27632. Representative Western blots are shown.

All values are means+/−SEM of three independent experiments. Individual dots represent the results of measurements from a single clone shown as a mean of three independent experiments; Ctr, Control; TR2, TRAIL-R2; mut, mutated; WT, wild type; ns, not significant; * $P<0.05$,  $P<0.01$ and * $p<0.0001$ Student's t-test (FIG. 7A) or ANOVA.

FIGS. 8A-8J| Autocrine TRAIL is required for caspase-independent migration and Rac1 activation. FIG. 8A, DLD-1 cells were transfected with the indicated siRNAs and subjected to migration assays. FIG. 8B, A549 cells were treated with DMSO or 10 µM zVAD-fmk and were subsequently subjected to migration assays. FIG. 8C, Dominant negative FADD (dnFADD)-overexpressing DLD-1 cells were transfected with the indicated siRNAs and subjected to migration assays. FIG. 8D, Parental and DLD-1 cells overexpressing dnFADD were treated with 1 µg/ml iz-TRAIL for the indicated times, subsequently lysed and subjected to Western blot analysis. FIG. 8E, A549 cells were treated with iz-TRAIL (100 ng/ml) for the indicated times and subjected to pulldown of GTP-bound Rac1 using PAK1-beads (Millipore-Rac1 activation kit). Cell lysates were subsequently analyzed by Western blotting. FIG. 8F, Control or shTRAIL-R2-infected A549 cells were subjected to pulldown of GTP-bound Rac1 as in FIG. 8E. FIG. 8G, A549 cells were transfected with the indicated siRNAs and subjected to migration assays. FIG. 8H, KRAS-mutated (DLD-1, HCT116) and isogenic KRAS-WT (DKO4, Hkh-2) cell lines were lysed and subjected to Western blotting. FIG. 8I, KRAS-mutated H460 cells were transfected with the indicated siRNAs. 48 h after transfection, the cells were lysed and subjected to Western blotting. FIG. 8J, KRAS-WT H522 cells were transfected with the indicated siRNAs, treated with vehicle ($H_2O$) or 10 µM Y27632 and subjected to migration assays.

Asterisk indicates non-specific band. Representative Western Blots are shown. All figures show means of three independent experiments +/−SEM; Ctr, Control; ns, not significant; * $P<0.05$,  $P<0.01$ and * $p<0.0001$ Student's t-test (FIG. 8B) or ANOVA.

EXAMPLE 1: KRAS-MEDIATED TRANSFORMATION REQUIRES ENDOGENOUS TRAIL/TRAIL-R2

Oncogenic mutation of KRAS is a hallmark of some of the most aggressive human cancers (Hidalgo, 2010; Jaffee et al., 2002; Mitsuuchi and Testa, 2002; Phipps et al., 2013). The aggressive behaviour of KRAS-mutated cancers can be attributed to their inherent chemo-resistance, strong invasiveness and capacity to metastasise (Downward, 2003), traits which render these cancers very difficult to treat (Chaffer and Weinberg, 2011). However, the effector mechanisms mediating invasiveness and metastasis of KRAS-mutated cancers are only incompletely understood and, importantly, have so far escaped therapeutic intervention. Here we show that oncogenic KRAS relies on endogenous TRAIL/TRAIL-R2 for transformation. The entire gain-of-migration afforded by oncogenic over wild-type (WT) KRAS was neutralised by TRAIL-R2 absence. In vivo, TRAIL-R2 absence from tumour cells or systemic inhibition of TRAIL significantly reduced experimental metastasis of KRAS-mutated cancer cells. In an autochthonous model of KRAS-driven pancreatic intraepithelial neoplasia (PanIN), the cancer-cell-restricted deletion of murine TRAIL-R (mTRAIL-R) resulted in substantial reduction of PanIN formation. Strikingly, cancer-cell-restricted genetic depletion of mTRAIL-R almost completely abrogated metastasis and resulted in a striking increase in overall survival time of mice that develop autochthonous KRAS/p53-driven pancreatic ductal adenocarcinoma (PDAC). Mechanistically, endogenous TRAIL/TRAIL-R2 signalling co-operated with mutated KRAS to activate Rac1 and, consequently, migration and metastasis. We have thus identified TRAIL/TRAIL-R2 signalling as a novel effector mechanism required for KRAS-driven transformation and metastasis. Importantly, this pathway is amenable to therapeutic intervention, for example by inhibition of TRAIL. We therefore anticipate that, based on our findings, new therapies for KRAS-mutated cancers can be devised.

Results

Increased migration and resistance to apoptosis are hallmarks of cellular transformation in cancer (Hanahan and Weinberg, 2011). KRAS-mutated colorectal cancer cells are resistant to apoptosis induction and exhibit increased migration when exposed to exogenous TRAIL (Hoogwater et al., 2010). Interestingly, many cancers constitutively express high levels of TRAIL-R1, TRAIL-R2 and TRAIL (Daniels et al., 2005; Ganten et al., 2009; Macher-Goeppinger et al., 2009; Ozawa et al., 2001; Sanlioglu et al., 2007; Spierings et al., 2003), and Ras-mediated transformation has been shown to coincide with increased expression of TRAIL-R1 and TRAIL-R2, amongst many other genes (Bild et al., 2006). However, whether oncogenic transformation by mutated KRAS and high expression of TRAIL/TRAIL-Rs are causally and functionally linked is currently unknown.

To test this hypothesis, we first compared the effect of suppression of TRAIL-R1 or TRAIL-R2 expression on migration in a panel of cancer cell lines with endogenous oncogenic KRAS mutations (FIG. 1A) which all expressed TRAIL-R1 and TRAIL-R2 (FIG. 2A). Silencing of neither TRAIL-R1 nor TRAIL-R2 had any discernible effect on proliferation of the cell lines tested (FIG. 2B). However, transient or stable knockdown of endogenous TRAIL-R2 (FIGS. 2C and 2D), but not TRAIL-R1, significantly diminished migration of all KRAS-mutated cancer cell lines tested, irrespective of tissue of origin (FIG. 1A and FIGS. 2C and 2D).

Since endogenous TRAIL-Rs are also expressed on KRAS-WT cell lines, we determined the migratory capacity, with and without TRAIL-R2 or mTRAIL-R (the murine homologue for both human TRAIL-Rs with a death domain, i.e. human TRAIL-R1 and TRAIL-R2 (Wu et al., 1999)), in a panel of cancer cell lines bearing either mutated or WT KRAS. Strikingly, cancer cells expressing oncogenic KRAS migrated significantly less when expression of endogenous TRAIL-R2 or mTRAIL-R was suppressed (FIG. 1B; for the list of cell lines and specific effects on migration in each one, see Supplementary Table 1). Intriguingly, the suppressive effect of TRAIL-R2 knockdown on migration was almost identical to the effect of KRAS knockdown (FIG. 1C), and knockdown of mTRAIL-R substantially reduced migration of a murine KRAS-mutated pancreatic cancer cell line (DT8082) by more than 90%, but not of a murine cell line generated from a DMBA/TPA-induced skin carcinoma containing an activating mutation in codon 61 of HRAS (DT02) (Grosse-Wilde et al., 2008) (FIGS. 2E and 2F). Incidentally, in the HRAS-driven DMBA/TPA-induced skin carcinoma model mTRAIL-R did not promote metastasis but suppressed it via its pro-apoptotic function (Grosse-Wilde et al., 2008). Together, this suggests that oncogenic KRAS, but not HRAS, specifically engages endogenous TRAIL-R2/mTRAIL-R to mediate migration.

To test this we used an established model of isogenic colon carcinoma cell lines which contained either mutated or WT KRAS (Shirasawa et al., 1993). Strikingly, the entire gain-of-migration afforded by oncogenic KRAS depended on endogenous TRAIL and TRAIL-R2, because knockdown of endogenous TRAIL-R2 suppressed migration to the same extent as absence of oncogenic KRAS (FIG. 1D) and knockdown of TRAIL (FIG. 1E) or its inhibition using a TRAIL-R2-Fc fusion protein suppressed migration to a similar extent (FIG. 1F).

Once cancer cells lose contact with the primary tumour, they have to survive anchorage-independently (Hanahan and Weinberg, 2011). Stable knockdown of TRAIL-R2, but not TRAIL-R1, significantly reduced colony formation in soft agar (FIG. 1G). Moreover, colonies formed by TRAIL-R2-stable-knockdown cells exhibited a less invasive phenotype (FIG. 1H). Hence, all KRAS-mediated traits of cellular transformation required for metastasis that can be determined in vitro appear to rely on autocrine TRAIL/TRAIL-R2.

We next aimed to assess the in-vivo relevance of these findings in regards to a possible role for endogenous TRAIL/TRAIL-R2 in cell-autonomous migration and metastasis of KRAS-mutated cancers. To do this, we first employed an experimental metastasis model using the human cancer cell line A549-luc with normal or suppressed expression of TRAIL-R2. Suppression of endogenous TRAIL-R2 resulted in a dramatic reduction of metastatic burden as determined by bioluminescence in-vivo imaging (FIG. 3A), histological inspection (FIG. 4A) and overall reduced lung size (FIG. 4B), without affecting luciferase activity (FIG. 4C). Because this effect was already discernible after one week (FIG. 4D), and because neither proliferation (FIG. 3B) nor cell death were affected by TRAIL-R2 absence from cells that formed metastasis (FIG. 3C), we conclude that TRAIL-R2 is required for an early step in the metastatic cascade of KRAS-mutated cancer cells.

This was further corroborated by the finding that subcutaneous growth of A549-luc cells was not affected by absence of TRAIL-R2 (FIGS. 4E and 4F). Together, these results pointed towards impaired invasiveness and migration, rather than decreased proliferation, as causative for reduced metastasis when TRAIL/TRAIL-R2 signalling is abrogated in this model. Importantly, treatment with the TRAIL-inhibiting TRAIL-R2-Fc fusion protein starting 1 day after injection of A549-luc cells (FIG. 4G) significantly reduced metastasis (FIG. 3D) to a similar extent as achieved by stable TRAIL-R2 suppression (FIG. 3A). Thus, endogenous TRAIL and TRAIL-R2 do not only promote key oncogenic traits of KRAS-mutated cancer cells in vitro but also their capacity to form metastases in vivo.

We next addressed whether endogenous TRAIL/TRAIL-R also affected development and progression of autochthonous KRAS-driven early and late stage cancer. KRAS is mutated in 95% of PDAC (Hidalgo, 2010; Jaffee et al., 2002) and a KRAS-mutated cell line derived from pancreatic tumours of KRAS$^{G12D}$xp53$^{R172H}$xPDX-1-Cre (KPC) mice employed mTRAIL-R for migration (FIG. 2E). Therefore, we set out to determine how mTRAIL-R deficiency (Grosse-Wilde et al., 2008), specifically in cancer cells, affected KRAS-driven pancreatic cancer. We first studied the effect of genetic depletion of mTRAIL-R on KRAS-driven PanIN formation in a mouse model recapitulating the early stage of pancreatic cancer development [KRAS$^{G12D}$xPDX-1-Cre (KC) mice] (Hingorani et al., 2003). We found that specific absence of mTRAIL-R from KRAS-transformed pancreatic cells markedly reduced the numbers of PanINs that developed in these mice (KC-mTRAIL-R$^{fl/fl}$) as compared to littermate controls (KC mTRAIL-R$^{wt/wt}$) (FIG. 5A, representative images shown in 5B). Hence, mTRAIL-R promotes KRAS-mediated PanIN formation, the precursor lesion of pancreatic cancer.

To investigate the role of mTRAIL-R in a mouse model that closely recapitulates the full spectrum of human pancreatic cancer, we made use of the established KPC mouse model of metastatic PDAC. This model utilizes conditional expression of KRAS$^{G12o}$ and p53$^{R172H}$ activated by PDX-1 promotor-driven Cre-recombinase that results in a mosaic pattern of combined KRAS$^{G12D}$/p53$^{R172H}$ expression in the adult pancreas, thereby inducing metastatic PDAC (Hingorani et al., 2005). The floxed mTRAIL-R alleles were successfully recombined in pancreata, but not tails or ears, of KPC-mTRAIL-R$^{fl/fl}$ mice (FIG. 6A). These mice were born at the expected Mendelian ratios and presented with a significant tumour burden starting at 5 weeks of age (data not shown). Absence of mTRAIL-R from KRAS/p53-double mutant pancreatic cancers dramatically increased the length of the lives of these mice (FIG. 5C) from a median of 112 days for KPC mTRAIL-R$^{wt/wt}$ mice to 162 days for KPC mTRAIL-R$^{fl/fl}$ mice. At the experimental endpoint all mice presented with abdominal distension, due to large pancreatic tumours and, in some cases, ascites accumulation (FIG. 6B). At respective time-of-death, sizes of pancreatic tumours were comparable between both groups (FIG. 6C), which was expected because KPC mTRAIL-R$^{fl/fl}$ mice lived significantly longer, leaving more time for primary tumours to develop and grow. Strikingly however, all KPC-mice that expressed mTRAIL-R in their tumour cells presented with distant lung metastasis at time-of-death whereas all but one of the mTRAIL-R$^{fl/fl}$ KPC-mice were metastasis-free at necropsy (FIG. 5D, representative images shown in FIG. 5E), despite living, on average, 50 days (i.e. 44%) longer than mice bearing mTRAIL-R-expressing tumours. This demonstrates that failure to metastasize in the absence of mTRAIL-R is not a consequence of smaller primary tumours at time-of-death but specifically disabled by absence of endogenous mTRAIL-R from KRAS-driven pancreatic cancer.

We previously showed that in HRAS-driven squamous skin cell carcinoma mTRAIL-R is a metastasis suppressor via its apoptosis-inducing function (Grosse-Wilde et al., 2008). Thus, depending on the oncogenic context which can favour apoptotic or pro-tumourigenic signalling of the endogenous TRAIL/TRAIL-R system, it can suppress or promote metastasis.

We next addressed which pathway downstream of mTRAIL-R/TRAIL-R2 could be responsible for increasing the migratory capacity of KRAS-mutated cancer cells and, consequently, for increased metastasis. We first turned to FADD and caspase-8 because they are the central components of canonical TRAIL signalling, as they are crucial for both, the TRAIL death-inducing signalling complex (DISC) (Sprick et al., 2000) and a secondary complex that forms subsequently to the DISC (Varfolomeev et al., 2005). Yet, neither caspase-8 knockdown nor pan-caspase inhibition significantly affected migration of KRAS-mutated cancer cells (FIGS. 8A and 8B). Also, neither overexpression of functional dominant-negative FADD (dnFADD) (FIGS. 8c and 8D), nor genetic deletion of FADD in three independent clones of A549 cells prevented migration reduction by TRAIL-R2 knockdown (FIG. 7A). Thus, autocrine TRAIL/TRAIL-R2-mediated migration is independent of FADD and caspase-8. Because FADD is also the adaptor protein for caspase-10 and cFLIP (Kischkel et al., 2000; Kischkel et al., 2001; Sprick et al., 2002; Sprick et al., 2000), these results imply that autocrine TRAIL/TRAIL-R2-mediated migration is also independent of these factors.

When inspecting the morphology of cells with stably suppressed TRAIL-R2 expression we noted that they presented with a more rounded morphology and less lamellipodia than control cells (FIG. 7B). Intriguingly, the small GTPase Rac1 is known to be required for lamellipodia formation, to be predominantly activated by KRAS as compared to HRAS (Walsh and Bar-Sagi, 2001), and Rac1 inhibition decreases the number and size of colonies grown in soft agar (Gao et al., 2004), reminiscent of absence of TRAIL-R2 (FIGS. 1G and 1H). Also, KRAS-driven PanIN formation was recently shown to depend on Rac1-mediated actin reorganisation without affecting proliferation (Heid et al., 2011). We therefore next tested whether Rac1, as compared to other KRAS effector pathways, would be required for mediating cell-autonomous migration in a TRAIL/TRAIL-R2-dependent manner. Because only inhibition of Rac1, but not of MEK or PI3Kα, resulted in significant reduction in migration similar to TRAIL-R2 knockdown (FIG. 7C), we next investigated whether TRAIL could potentially activate Rac1. Indeed, TRAIL was able to activate Rac1 in A549 cells (FIG. 8E), and basal activation of Rac1 was reduced in the absence of endogenous TRAIL-R2 (FIG. 8F). The fact that knockdown of Rac1, in addition to knockdown of TRAIL-R2, did not result in further reduction of migration (FIG. 7D), indicates that Rac1 and TRAIL-R2 form part of a single pro-migratory pathway, rather than parallel pathways that can compensate for each other.

Rac1 activity is kept in check by RhoA-induced ROCK activation (Sanz-Moreno et al., 2008). In line with this, suppression of RhoA increased migration (FIG. 8G). This effect could, however, be completely reversed by co-suppression of TRAIL-R2 (FIG. 8G). Since migration mediated by oncogenic but not WT KRAS employed endogenous TRAIL-R2 (FIG. 1B), we next tested TRAIL's capacity to activate Rac1 in isogenic KRAS-mutated versus -WT cells. We found that TRAIL was only capable of doing so in KRAS-mutated cells (FIG. 7E). Thus, TRAIL-induced Rac1 activation is specifically enabled in cancer cells expressing oncogenic KRAS. This explains why Rac1-driven migration is not reduced by TRAIL-R2 suppression in KRAS-WT cells.

We next aimed to identify which signalling pathway downstream of oncogenic KRAS enabled TRAIL/TRAIL-R2 to activate Rac1. As KRAS-mutated cancer cells are rendered resistant to TRAIL-induced apoptosis via suppression of the ROCK/LIMK/cofilin pathway (Hoogwater et al., 2010), we reasoned that oncogenic KRAS-mediated ROCK suppression might remove this constraint on Rac1 activation. If this were the case, pharmacological inhibition of ROCK in KRAS-WT cells should enable TRAIL/TRAIL-R2 to activate Rac1 and, consequently, migration of these cells. Basal phosphorylation of cofilin, downstream of ROCK/LIMK, was indeed decreased in KRAS-mutated as compared to isogenic WT counterparts (FIG. 8H). Likewise, transient knockdown of KRAS in KRAS-mutated cells increased phosphorylation of cofilin (FIG. 8I). Indeed, ROCK inhibition mimicked presence of oncogenic KRAS in WT cells and enabled endogenous TRAIL-R2 to increase migration; strikingly, the entire increase by ROCK inhibition was prevented by TRAIL-R2 knockdown (FIG. 7F). Yet, knockdown of KRAS did not reverse ROCK-inhibition-induced migration in KRAS WT cells (FIG. 8J). Thus, oncogenic KRAS acts upstream and TRAIL/TRAIL-R2 downstream of ROCK inhibition in Rac1-dependent migration. Therefore, ROCK-inhibition by other means than KRAS-mutation is sufficient to enable TRAIL-R2 to signal migration.

We show here that stimulation of TRAIL-R2/mTRAIL-R by endogenous autocrine TRAIL promotes KRAS-mediated transformation, that KRAS-mutated cancers employ endogenous TRAIL/mTRAIL-R to accelerate PanIN formation and that PDAC metastasis depends on endogenous TRAIL/mTRAIL-R. Our mechanistic data suggests that suppression of ROCK by oncogenic KRAS, that can be mimicked by pharmacological ROCK-inhibition, is a prerequisite for Rac1 activation by autocrine stimulation of TRAIL-R2/mTRAIL-R to drive cancer cell migration and, consequently, PanIN formation and metastasis. Our study provides novel insight on the biology of KRAS-driven carcinogenesis and, additionally, a new rationale for therapeutically disarming KRAS-mutated cancers, namely by inhibiting (the pro-tumourigenic activities of) TRAIL/TRAIL-R2.

Methods Summary siRNA-mediated knockdown. Knockdown experiments were performed by transient transfection of RISC-free control siRNA, siRNA pools or single sequences (Dharmacon) to silence the indicated proteins using Dharmafect I (Dharmacon) following the instruction manual. All cell lines were incubated for 48 h to achieve sufficient knockdown.

Migration assays. Migration assays were performed using the xCELLigence System (Roche) according to manufacturer's instructions. See Supplementary Methods for detailed description.

Animal Models. Experimental metastasis: 12-week old female Fox Chase® SCID Beige Mice (Charles River, Germany) were injected with 2×106 A549-luc vector control or shTRAIL-R2 cells via the lateral tail vein. Starting on day 1 after cell injection, all mice were imaged weekly for bioluminescence using the Ivis Spectrum (Caliper Life Science). Photons per second (Photon Flux) were quantified using the Ivis Spectrum software. Vehicle or TRAIL-R2-Fc were administered at 500 µg/mouse i.p. as indicated (Supplementary FIG. 2g). Subcutaneous tumours: 8-week-old female Fox Chase® SCID Beige Mice (Charles River, Germany) were injected subcutaneously with 1.5×106 A549-luc vector control or shTRAIL-R2 cells resuspended in 150 µl DPBS/Matrigel (50:50) (BD Bioscience) in both flanks. After one week, tumours were palpable and their size was measured by caliper. Tumor volume=0.52×width× length2. KC/KPC-mTRAIL-R mice: KRASG12D, p53R172H and PDX-1-Cre mice on C57BL/6 background were kindly provided by D. Tuveson, mTRAIL-Rfl/fl mice on C57BL/6 background were previously generated by our laboratory (Grosse-Wilde et al., 2008). PDX-1-driven expression of Cre-recombinase results in a mosaic Cre-expression pattern (Hingorani et al., 2003) that exises mTRAIL-R in the same cells that are concomitantly activated to express $KRAS^{G12D}$ (KC model) or $KRAS^{G12D}$ and $p53^{R172H}$. All mice were kept under an appropriate UK project licence.

Material and Methods

Reagents

Antibodies: α-FADD was purchased from BD Bioscience, α-KRAS from Santa Cruz, α-β-Actin from Sigma, α-Rac1 and α-Rho from Millipore, α-TRAIL-R2, α-pCofilin, α-Cofilin, from Cell Signalling, α-Caspase-8 as described (Scaffidi et al., 1997), α-TRAIL from Alexis and α-TRAIL-R1 was purchased from ProSci, α-mTRAIL-R was produced in our laboratory. HS101, HS201, H301 and H402 were used for surface staining of TRAIL-R1 to TRAIL-R4 and are available from Alexis. Recombinant proteins: DR6-Fc, TRAIL-R2-Fc and TNF-R2-Fc were purified from supernatants of transfected HEK293T cells via protein A columns (GE Healthcare), iz-TRAIL was produced in E. coli, purified as described previously (Ganten et al., 2006), iz-TRAIL was LPS-free after purification as tested by Limulus amebocyte lisate (LAL) assay (LONZA). PD98059, NSC23766, Y27632 were purchased from Calbiochem and PIK75 was purchased from Selleck Chemicals.

Cell Lines

Isogenic colorectal cancer cell line pairs DLD-1/DKO4 and HCT116/Hkh-2 (Shirasawa et al., 1993) and DLD-1 dnFADD were kindly provided by O. Kranenburg, pancreatic cancer cell lines Panc Tu I and Colo357 were kindly provided by A. Trauzold, murine $KRAS^{G12D}/p53^{R172H}$ cell line DT8082 was kindly provided by D. Tuveson, the human lung adenocarcinoma panel of KRAS-mutated and WT cell lines (H460, H520, H522, H322) was kindly provided by J. Downward, A549-luc cells were purchased from Caliper Life Science and murine HRAS-mutated skin carcinoma cell line DT02 was previously generated in our laboratory (Grosse-Wilde et al., 2008). DLD-1, DKO4, HCT116, Hkh-2 and DLD-1 dnFADD cells were cultured in DMEM supplemented with 10% FCS and 2 mM Glutamine, DT8082 and DT02 cells were cultured in DMEM supplemented with 10% FCS, Panc Tu I and Colo357 were cultured in RPMI1640 supplemented with 10% FCS, 2 mM Glutamine and 1 mM sodium pyruvate and the human lung cancer cell line panel including A549-luc cells were cultured in RPMI1640 supplemented with 10% FCS.

Migration Assays

Migration assays were performed using the xCELLigence System (Roche) that uses specially designed microtiter plates containing gold microelectrodes to measure electrical impedance of cells adhering to electrodes in real time. Increased impedance of background control wells was subtracted from all other values, the increase in electrical impedance/migration of control siRNA-transfected/control vector-infected cells was then defined as 100% migration and relative migration of all other transfected samples was calculated as compared to control-transfected cells, accordingly. Migration plates (CIM 16) are based on the Boyden chamber principle, the lower surface of the filter is covered with microelectrodes measuring cells that have migrated through the pores and adhere to the lower surface of the filter in real time. Briefly, the lower chambers of a CIM 16 plate were filled with media containing 2% FCS as chemoattractant, the upper part was assembled and 30 µl of FCS-free medium was added to the top wells. The plate was then equilibrated in the incubator for 1 h. Cells were trypsinized and washed three times in FCS-free medium. Then, $8 \times 10^5$ cells were resuspended in 1 ml FCS-free medium and 100 µl cell suspension was added to each well after a background measurement without cells was performed. Four wells without cells (FCS-free medium only) were included as assay background control. Cells were left to settle in the top well of the plates at room temperature for 30 minutes and then plates were returned to the RTCA-DP xCELLigence system and impedance measurements were taken every minute. Cells that had been transfected with siRNA were left to migrate for a total of 6 h and stable shRNA-infected cells for a total of 12 h.

Soft Agar Assays

Growth of cells in soft agar was determined using the Cell Transformation Detection Assay (Millipore). 500 µl of 0.8% noble agar in sterile H2O/medium 1:2 was used per one 24-well. Bottom agar was allowed to set for 20 minutes at 4° C. Meanwhile, cells were washed with DPBS, trypsinised and filtered through 40 µM filters to obtain a single cell solution. 10000 cells per 24-well were mixed with 250 µl 0.4% top agar (bottom agar further diluted in medium) and immediately placed on top of the pre-warmed bottom agar. After the top agar gel had set, 250 µl medium was placed on top. Cells were left to form colonies for 4 weeks, stained using the Cell Stain Solution provided by the kit, and all colonies were counted.

TRAIL-R Surface Staining

Cells were detached using Accutase (Sigma) and counted. 2×105 cells were incubated with 10 µg/ml anti-TRAIL-R1, -R2, -R3 and -R4 (HS101, HS201, HS301 and H5402) or IgG1 isotype control antibody in 2% BSA in PBS (BSA/PBS) for 30 minutes on ice. Cells were washed twice with ice-cold BSA/PBS before incubation with secondary goat-anti-mouse-APC (BioLegend) at a dilution of 1:200 in BSA/PBS for 20 minutes on ice. Cells were washed three times in ice-cold BSA/PBS and surface expression was assessed by flow cytometry.

Western Blot Analysis

Cells were treated as indicated and then lysed in IP-lysis buffer (30 mM Tris-HCl [pH 7.4], 120 mM NaCl, 2 mM EDTA, 2 mM KCl, 1% Triton X-100, 1×COMPLETE protease-inhibitor cocktail) at 4° C. for 30 min. Proteins were separated by SDS-PAGE (NuPAGE) and analyzed by Western blotting. Membranes were stripped with 50 mM glycine (pH 2.3) before reprobing with other antibodies.

Generation of cells expressing shRNA targeting TRAIL-R1 and TRAIL-R2 A549-luc/DLD-1cells were seeded at 500.000 cells into 25 cm2 flasks. The following day, they were infected with 1:2 medium-diluted lentivirus supernatant containing sequences for either the vector (pIKO.1) or five different shRNA sequences for human TRAIL-R1 or human TRAIL-R2, respectively. All sequences were purchased from Sigma. After 48 h incubation with the virus, cells were subjected to selection with 2 µg/ml puromycin for 2 weeks. Afterwards, selected cells were subjected to Western blot in order to analyze for the levels of TRAIL-R suppression. For TRAIL-R1, the sequence CCGGCTTAG-GTGTTAGGAGTTAATACTCGAGTATTAACTC- CTAACACCTAAGTTTTT (SEQ ID NO: 1)(Sigma Cat nr. TRCN0000005934) (shTRAIL-R1) generated sufficient knockdown as compared to vector-infected cells and cells infected with this sequence were therefore chosen for further analysis. For TRAIL-R2, only the sequence CCGGGCA-GAAGATTGAGGACCACTTCTCGAGAAGTGGTCCT-CAATCTTCTGCTTTTT (SEQ ID NO: 2)(Sigma Cat nr. TRCN0000005933) (shTRAIL-R2) generated sufficient suppression of TRAIL-R2 expression and cells infected with this sequence were therefore also chosen for further analysis. Sigma Cat nr. TRCN0000005930 sequence targeting TRAIL-R2 did not result in significant knockdown in A549 cells and were used as shRNA control (shCtr).

Generation of FADD Knockout Cell Lines

A549-luc cells were transfected with 5 µl mRNA encoding a Zinc Finger Nuclease targeting FADD (CompoZr®, Sigma-Aldrich) using Lipofectamine 2000 (Invitrogen). The Zinc Finger Nuclease generates DNA double strand breaks that upon non-homologous end-joining in some cases results in disruption of the gene producing a knockout. Subsequently, single cells were seeded into 96-well plate in RPMI growth medium supplemented with 10% FCS and 30% conditioned medium. After two weeks, single cell colonies were selected and subsequently seeded into 12-well plate for further expansion. After an additional week, cells grown from a single cell clone were lysed and screened by Western Blotting for the presence or absence of FADD.

Rac1 Pulldown Assays $2.5 \times 10^6$ cells were seeded into 10 cm dishes. The next day, cells were incubated with and without 100 ng/ml iz-TRAIL. Cell lysis and Rac1 pulldown was performed using a Rac1-pulldown kit (Millipore) according to the manufacturer's instructions. Proteins were separated by SDS-PAGE (NuPAGE) and analyzed by Western blotting.

Confocal Analysis

Cells were seeded on poly-Lysine-coated microscopic coverslips at $2.5 \times 10^4$ cells/24-well. The following day, cells were treated as indicated, then fixed for 10 minutes in 5% formaldehyde, subsequently permeabilized (in PBS containing 0.02% Triton-X 100 and 1% BSA for 5 minutes) and blocked (in 1% BSA for 1 hour). Texas-Red coupled Phalloidin (Invitrogen, Molecular Probes) was used at 5 µl/200 µl blocking buffer as suggested by the manufacturer and incubated for 30 minutes at RT in the dark. Subsequently, the cells were washed three times with PBS, and Phalloidin-stained coverslips were mounted in DAPI (ProLong® Golds antifade reagent with DAPI, Invitrogen). Images were acquired at ×400 magnification using a confocal microscope and software (Leica).

BrdU Proliferation Assay 24 h after cells had been subjected to transient knockdowns as described in Experimental procedures, BrdU stock (Cell proliferation assay kit, Calbiochem) was added at a dilution of 1:2000 in medium and incubated for another 24 h. Then, the BrdU proliferation assay was performed according to the manufacturer's instructions.

Luciferase Assay

Stable A549-luc knockdown cells were seeded at the indicated numbers in 96-well plates. The following day, medium was removed and cells were permeabilized with 30 µl of Permeabilization Buffer (eBioscience) for 15 minutes. Subsequently, 30 µl Firefly luciferin-containing buffer (Luciferase Assay buffer) was added and incubated for 10 minutes. The relative luminescence was determined using a Mithras plate reader.

Immunohistochemistry (IHC)/Immunofluorescence (IF)

For preparation of lung tissue sections, mice were sacrificed 3.5 weeks after cell injection according to Guidance on Operation of Animals [Scientific Procedures] Act 1986. From each mouse the upper lobe of the left lung was removed, fixed in 10% formalin (Sigma) for one week and then transferred to 70% ethanol. Paraffin embedding, preparation of sections and H&E stainings were performed as part of a histological staining service the National Heart & Lung Institute. Paraffin sections were stained for Ki67 (Dako) at a 1/80 dilution and CK19 (AHP1846, Serotec) at 5 µg/ml. Sections were de-waxed and rehydrated by passing the slides through xylene and descending grades of alcohol then rinsed in water. The slides were incubated for 15 minutes with 0.6% hydrogen peroxide solution for IHC. Slides were rinsed and immersed in 0.1 M citrate buffer (pH 6.0) and microwaved for 15 minutes (750 watts) for antigen retrieval. Slides were then immediately cooled under running water and rinsed in phosphate buffered solution (PBS). 100 µl of Protein Block was added to each slide for 5 minutes. After rinsing with 0.05% PBS/Tween 20 solution for 5 minutes, the slides were incubated with 100 µl of the primary antibody at 4° C. overnight. Following overnight incubation, slides were washed with 0.05% PBS/Tween 20 solution. The sections were then incubated with secondary antibody for 30 minutes (IHC) or 1 h (IF) at room temperature and again washed three times. The sections were developed using the ABC kit (Vector laboratories) before being counterstained by haematoxylin for 2 minutes and rinsed in water for 5 minutes for IHC.

Slides were then dehydrated in ascending grades of alcohol and cleared in 3 changes of xylene (IHC). Finally, the sections were mounted using Di-N-Butyle Phthalate in Xylene (DPX) mounting solution and covered with a glass coverslip (IHC) or mounted in DAPI (ProLong® Golds antifade reagent with DAPI, Invitrogen) (IF). For negative controls, duplicate slides from each case were used. These slides were incubated with 100 µl antibody diluent instead of primary antibody/secondary antibody. H&E stainings were examined by an experienced pathologist (Mona A. El-Bahrawy) who was blinded to the study. TUNEL assay was performed using the TACS.XL®-Blue Label in Situ Apoptosis Detection Kit according to the manufacturer's instructions (Trevigen). Tumor burden was quantified as percentage of tumor tissue in the lung, Ki67 and TUNEL positive cells as percentage of cells within tumor nodules.

Animal Husbandry

All mice were maintained in individually ventilated cages (IVCs), SCID beige mice received autoclaved food, water and bedding according to institutional guidelines under a UK Home Office project license. The required risk assessments were obtained for this study.

SUPPLEMENTARY TABLE 1

TRAIL-R2 knockdown-mediated migration reduction in a comparative panel of KRAS-mutated and -WT cell lines.

|  | cancer origin | TRAIL-R2 KD [% migration reduction] |
|---|---|---|
| KRAS-WT |  |  |
| DKO4 | Colorectal | −0.3 |
| Hkh-2 | Colorectal | 18.1 |
| H520 | Lung | 14.5 |
| H522 | Lung | 27.3 |
| H322 | Lung | 50.0 |

SUPPLEMENTARY TABLE 1-continued

TRAIL-R2 knockdown-mediated migration reduction in a comparative panel of KRAS-mutated and -WT cell lines.

| | cancer origin | TRAIL-R2 KD [% migration reduction] |
|---|---|---|
| KRAS-mutated | | |
| DLD-1 | Colorectal | 49.0 |
| A549 | Lung | 51.3 |
| H460 | Lung | 41.9 |
| Panc Tu 1 | Pancreatic | 53.4 |
| Colo357 | Pancreatic | 82.4 |
| DT8082* | Pancreatic | 97.0 |

KD = transient knockdown;
WT = wild-type;
*murine.

EXAMPLE 2: CONSTRUCTION OF FUSION PROTEIN

A fusion protein was constructed consisting of the majority of the extracellular domain of humanTRAIL-R2 fused to the Fc portion of human IgG1, containing a portion of the hinge domain, the CH2 domain and the CH3 domain of human IgG1.

The human IgG1 Fc domain sequence is from: Ellison, J.,"The nucleotide sequence of human immunoglobulin C gene", Nucleic Acid Research, Volume 10 Number 13, 1982. cDNA was created from total RNA isolated from Peripheral Blood Lymphocytes (PBL) from donor blood by RT-PCR using Oligo dT primer. A PCR was used to amplify the cDNA of human IgG1 Fc (partial hinge plus CH2 plus CH3) with an overlapping sequence to TRAIL-R2 in the sense primer (underlined and in bold in the sense primer sequence) and an EcoRI site (underlined in the below antisense primer sequence) following the stop codon (in bold in the below antisense primer sequence) in the antisense primer.

```
Primer: Sense-huIgG1:
                                         (SEQ ID NO: 3)
cca ggg act cct gcc TCT TGT GAC AAA ACT CAC ACA TG
(Capital letters => part of huIgG1) If.

Primer: Antisense-EcoR1-huIgG1:
                                         (SEQ ID NO: 4)
TATA gaa ttc tca ttt acc cgg aga cag gg
```

The human TRAIL-R2 sequence is from Walczak et al. 1997, "TRAIL-R2: a novel apoptosis-mediating receptor for TRAIL" The EMBO Journal Vol. 16, No. 17, pp. 5386-5397, 1997 (Accession number DDBJ/EMBL/GenBank: AF016849).

As outlined in example 3 and 4, cDNA was created from total RNA isolated from Peripheral Blood Lymphocytes (PBL) from donor blood by RT-PCR using an Oligo dT primer. A PCR was used to amplify a portion of the cDNA of TRAIL-R2 by including a Hind III restriction site and a Kozak Sequence at the 5'-end (underlined in sense primer sequence below) of the sense primer preceding the start codon (printed in bold in the sense primer sequence below) and in the antisense primer an overlapping sequence to human IgG1 (one codon, encoding amino acid 207 (serine); printed in bold and underlined in the antisense primer sequence below].

```
Primer: Sense-HindIII-huTRAIL-R2:
                                         (SEQ ID NO: 5)
TATA aag ctt gcc gcc acc atg gaa caa cgg gga
cag aac Primer: Antisense-huTRAIL-R2:
                                         (SEQ ID NO: 6)
gtg agt ttt gtc aca aga GGC AGG AGT CCC TGG
(Capital letters => part huTRAIL-R2, in reverse)
```

Cloning Procedure: Following the amplification, a gel extraction was performed to isolate the modified inserts. Then a third PCR utilizing both fragments was performed. Due to the overlap of both fragments and the primers at the end, this PCR joins in one product. Afterwards the product was digested with Hind III and EcoR I and ligated in a suitable expression vector, in this case pcDNA3.1 (Invitrogen).

```
Primer: Sense-HindIII-huTRAIL-R2
                                         (SEQ ID NO: 7)
TATA aag ctt gcc gcc acc atg gaa caa cgg gga
cag aac Primer: Antisense-EcoRI-huIgG1
                                         (SEQ ID NO: 8)
TATA gaa ttc tca ttt acc cgg aga cag gg
```

Expression of the TRAIL-R2-Fc Fusion Protein:

HEK293T cells were transfected by $CaCl_2$ transfection method with the above outlined pcDNA3.1-based expression vector for TRAIL-R2-Fc (pcDNA3.1-TRAIL-R2-Fc). Recombinant protein-containing cell culture supernatants were harvested after 48 h, 72 h and 96 h. These fractions were pooled, filtered (0.2 μm) and affinity purified via protein A columns (GE Healthcare).

EXAMPLE 3: AMINO ACID SEQUENCE OF TRAIL-R2 (SEQ ID NO: 9)

The extracellular domain of mature (i.e. without the leader sequence) TRAIL-R2 is shown in bold. The portion of the extracellular domain contained in the mature TRAIL-R2-Fc protein is underlined. The difference between the mature and immature TRAIL-R2 is the leader peptide for human TRAIL-R2, according to Walczak et al. (www.uniprot.org/blast/?about=O14763[56-210]). The exact position of the N terminus can vary by a few amino acids; that means the mature protein can be, e.g. three to five amino acids shorter or longer.

```
          10          20          30          40
MEQRGQNAPA  ASGARKRHGP  GPREARGARP  GPRVPKTLVL 50          60          70          80
VVAAVLLLVS  AESALITQQD  LAPQQRAAPQ  QKRSSPSEGL 90         100         110         120
CPPGHHISED  GRDCISCKYG  QDYSTHWNDL  LFCLRCTRCD 130         140         150         160
SGEVELSPCT  TTRNTVCQCE  EGTFREEDSP  EMCRKCRTGC 170         180         190         200
PRGMVKVGDC  TPWSDIECVH  KESGTKHSGE  VPAVEETVTS 210         220         230         240
SPGTPASPCS  LSGIIIGVTV  AAVVLIVAVF  VCKSLLWKKV 250         260         270         280
LPYLKGICSG  GGGDPERVDR  SSQRPGAEDN  VLNEIVSILQ
```

```
              290        300        310        320
PTQVPEQEME VQEPAEPTGV NMLSPGESEH LLEPAEAERS 330        340        350        360
QRRRLLVPAN EGDPTETLRQ CFDDFADLVP FDSWEPLMRK 370        380        390        400
LGLMDNEIKV AKAEAAGHRD TLYTMLIKWV NKTGRDASVH 410        420        430        440
TLLDALETLG ERLAKQKIED HLLSSGKFMY LEGNADSAMS
```

EXAMPLE 4: NUCLEOTIDE AND AMINO ACID SEQUENCE (FROM WALCZAK ET AL. 1997)

(SEQ ID NOs: 10 and 11, respectively)

```
  1      GAATTCGCGGACACCGCTCATAAATCAGCCACGCGGCCGGAGAACCCCGAGATGCCGATCTACTTTAAGGCTGAAACCCACGGGCCTGAGAG                                                                    120
121      ACTATAAGAGCCGTTCCCTACCGCCATGGAACACAGAACGGGACACGGCCGAAAAGGCACGGCCCCAGGAGCGCGGGAGCCAGGCCCCAGGAGCCC                                                                   240
  1                              M  E  Q  R  G  Q  N  A  P  A  A  S  G  A  R  K  R  H  G  P  R  E  A  R  G  A  R  P  G  P                                         72

241      CGGGGTCCCCAAGACGCTTGTCCTCGTTGTCGCCGCCGTGCTCTGTGTTGGTCTCAGTCGAGTCTGATCATCCAACAGAGACTAGCTCCCCAGAGCGGCCCACACAAGAGAG                                                         360
 73      R  V  P  K  T  L  V  L  V  V  A  A  V  L  L  V  S  A  E  S  A  L  |I  T  Q  Q  D  L  A  P  Q  Q  R| A  A  P  Q  Q  K                                       72
                                                                                                         ▲56

361      AGGTCCAGCCCCTCAGAGGATTGTCCACCTGAACACCATATCTCAGAGAACGGTAGAGATTGCATCTCTGCAAATATGGAACAGGACTATAGCACTCACTGGAATGACCTCTTTC                                                         480
 73      R  S  S  P  S  K  G  L  C  P  P  G  H  H  I  S  K  D  G  R  D  C  I  S  C  K  |Y  G  Q  D  T  S  T  H  W  N  D  L  L  F                                    112

481      TGCTTGCGCTGCACCAGGTGTGATTCAGGTGAAGTCAGGTGAAGTGGAGGTGAAGGCACCTTCCGGAAGAAGGCACCTTCCGGAAGAATTCTCCTGAGATG                                                                     600
113      C  L  R| C  T  K  |C  D  S  G  E  V  E  L  S  P  C  T  T  T  R| |N  T  V  C  Q  E  E  G  T  F  R  E  E  D  S  P  E  M                                        152

601      TGCCGGAAGTGCCGCACAGGGTGTCCCAGAGGATGGTGAAGGTCGGTCCGTGTGATTGTACACCCTGGAGTGACATCGAATGTGTCCACAAAGAATCAGGTACAAGCTACACAGTGGGAAGCCCA                                                720
153      C  R  K  C  R  T  G  C  P  R  G  M  V  K  |V  G  D  C  T  P  W  E  D  I  E  C  V  H  K| K  E  S  G  T  K  H  S  G  K  A  P                                  192

721      GCTGTGGAGGAGACGGTGACCTCCAGCCCAGGGACCCCAGCCCAGTGCAGCCTGTCAGCCGTAGTCTTGATTGTGGCTGTGTTGTTTGC                                                                               840
193      A  V  E  E  T  V  T  S  S  P  G  T  P  A  S  P  C  S  L  S  G  I  I  I  G  V  T  V  A  A  V  V  L  I  V  A  V  F  V  C                                      232

841      AAGTCTTTACTGTGGAAGAAAGTCCTTCCTTACCTGAAGGCATCTGCTCAGGTGGGGGGGGGACCCTGAGCGTGTGGAGACGTCACAGACCTCGGGCGCGAGGACAATGTCCTG                                                         960
233      K  S  L  L  W  K  K  V  L  P  Y  L  K  G  I  C  S  G  G  G  D  D  P  E  R  V  D  R  S  S  Q  R  P  G  A  E  D  N  V  L                                       272
```

```
961   AATGAGATCGTGAGTATCTTGCAGCCCACCCAGGTTCCCCTGAGCAGGAAATGGAAGTTCAAGAGCAGCCAGCCGAGCCGACCGGGGAGTCAGAGCATCTGCTG    108
273    N  E  I  V  S  I  L  Q  P  T  Q  V  P  E  Q  K  M  E  V  Q  E  P  A  E  P  T  G  V  N  M  L  S  P  G  E  S  E  H  L  L    312

1081  GAACCGGCAGAAGCTGAAAGTCTCAGAGGAGGAGGCTGTTCAGCACAAATGAAGTGAAGTGATCCCACTGAGACTCTGAGACTTGTGCCCTTTGAC            120
313    E  P  A  E  E  R  S  Q  R  R  L  L  V  P  A  N  E  G  D  P  T  E  T  L  R  Q  C  F  D  D  F  A  D  L  V  P  F  D            352

1201  TCCTGGGAGCCGCTCATGAGAAGTTGGGCCTCATGGACAATGAGATAAAGTGGTTAAAGCAGCAGGCACACGTCGCAGATGCTACGATAAAGTGGTCAACAAA    132
353    S  W  E  P  L  M  R  K  L  G  L  M  D  N  E  I  K  V  A  K  A  E  A  A  G  H  R  D  T  L  Y  T  M  L  I  K  W  V  N  K    392

1321  ACCGGGCGAGATGCCTCTGTCCACACCCTCCTGGATGCCTTGGAGACGCTGGGAGAGAGAATTGCCAAGCAGAAGATTGAGGACCACTTGTTGAGCTCTGAAGTTCATGTATCTAGAA    144
393    T  G  R  D  A  S  V  H  T  L  L  D  A  L  E  T  L  G  E  R  L  A  K  Q  K  I  E  D  H  L  L  S  G  K  F  M  Y  L  E    432

1441  GGTAATGCAGACTCTGCCATGTCCTAAGTGTGATTCTTCAGGAAGTGAGACCTTCCCTGGTTACCTTTTTTCTGAAAAAGCTGACTCCAGTCAGTAGGAAAGCTGCCACAA            156
433    G  N  A  D  S  A  M  S  *                                                                                                  441

1561  TTGTCACATGACCGGTACTGAAGAAACTCTCCCCATCCAACATCCCAGTGATGAAACATCCTGTAACTTTTCACTGCACTGGCATTATTTTTATAAGCTAAGGA                    168

1681  CACTATGGAAATGTCTGGATCATTCCGTTTGTGCTACTTTGAGATTTGAGATGCATTGTTTTCACAGCACTTTTTTATCCTAATGTAAATGCTTTATTATTTATTTGGCTA            180

1801  CATTGTAAGATCCAGGTCGTCTCGTTTCAAGATCTGTTTAAACTAGTTAGCTAGGC                                                                    1859
```

EXAMPLE 5: NUCLEOTIDE AND AMINO ACID SEQUENCE FOR TRAIL (SEQ ID NOs: 12 and 13, respectively)

```
Nucleotide: (www.ncbi.nlm.nih.gov/nuccore/CR456895.1)
  1    atggctatga tggaggtcca gggggaccc agcctgggac agacctgcgt gctgatcgtg
 61    atcttcacag tgctcctgca gtctctctgt gtggctgtaa cttacgtgta ctttaccaac
121    gagctgaagc agatgcagga caagtactcc aaaagtggca ttgcttgttt cttaaaagaa
181    gatgacagtt attgggaccc caatgacgaa gagagtatga acagccctg ctggcaagtc
241    aagtggcaac tccgtcagct cgttagaaag atgattttga aacctctga ggaaaccatt
301    tctacagttc aagaaaagca acaaaatatt tctccctag tgagagaaag aggtcctcag
361    agagtagcag ctcacataac tgggaccaga ggaagaagca acacattgtc ttctccaaac
421    tccaagaatg aaaaggctct gggccgcaaa ataaactcc gggaatcatc aaggagtggg
481    cattcattcc tgagcaactt gcacttgagg aatggtgaac tggtcatcca tgaaaaaggg
541    ttttactaca tctattccca aacatacttt cgatttcagg aggaaataaa agaaaacaca
601    aagaacgaca aacaaatggt ccaatatatt tacaaataca caagttatcc tgaccctata
661    ttgttgatga aaagtgctag aaatagttgt tggtctaaag atgcagaata tggactctat
721    tccatctatc aagggggaat atttgagctt aaggaaaatg acagaatttt tgtttctgta
781    acaaatgagc acttgataga catggaccat gaagccagtt ttttcgggc ctttttagtt
841    ggttaa
```

```
Amino acid: (www.uniprot.org/uniprot/P50591)
            10         20         30         40         50         60
    MAMMEVQGGP SLGQTCVLIV IFTVLLQSLC VAVTYVYFTN ELKQMQDKYS KSGIACFLKE 70         80         90        100        110        120
    DDSYWDPNDE ESMNSPCWQV KWQLRQLVRK MILRTSEETI STVQEKQQNI SPLVRERGPQ 130        140        150        160        170        180
    RVAAHITGTR GRSNTLSSPN SKNEKALGRK INSWESSRSG HSFLSNLHLR NGELVIHEKG 190        200        210        220        230        240
    FYYIYSQTYF RFQEEIKENT KNDKQMVQYI YKYTSYPDPI LLMKSARNSC WSKDAEYGLY 250        260        270        280
    SIYQGGIFEL KENDRIFVSV TNEHLIDMDH EASFFGAFLV G
```

EXAMPLE 6: THE AMINO ACID SEQUENCE OF THE TRAIL-R2-FC PROTEIN

The TRAIL-R2 portion is underlined. The Fc portion is depicted in bold. Note that there is a one amino acid overlap between TRAIL-R2 portion and the human IgG1 FC portion. The leader peptide is depicted in italics. The mature protein starts with the sequence ITQQDLA (According to Walczak et al., EMBO Journal 1997) (SEQ ID NO: 14). When produced recombinantly, the exact position of the N terminus can vary by a few amino acids; that means the mature protein can be, e.g. three to five amino acids shorter or longer.

*MEQRGQNAPAASGARKRHGPGPREARGARPGPRVPKTLVLVVAAVLL*

*LVSAESA*LITQQDLAPQQRAAPQQKRSSPSEGLCPPGHHISEDGRDC

ISCKYGQDYSTHWNDLLFCLRCTRCDSGEVELSPCTTTRNTVCQCEE

GTFREEDSPEMCRKCRTGCPRGMVKVGDCTPWSDIECVHKESGTKHS

GEVPAVEETVTSSPGTPASCDKTHTCPPCPAPELLGGPSVFLEPPKP

KDTLMISRTPEVTCVVVDVSHEDPEVKFNWYVDGVEVHNAKTKPREE

QYNSTYRVVSVLTVLHQDWLNGKEYKCKVSNKALPAPIEKTISKAKG

QPREPQVYTLPPSRDELTKNQVSLTCLVKGFYPSDIAVEWESNGQPE

NNYKTTPPVLDSDGSFFLYSKLTVDKSRWQQGNVFSCSVMHEALHNH

YTQKSLSLSPGK (SEQ ID NO: 15)

EXAMPLE 7: THE NUCLEOTIDE SEQUENCE ENCODING THE IMMATURE TRAIL-R2-FC PROTEIN (SEQ ID NO: 16)

atggaacaacggggacagaacgccccggccgcttcgggggcccggaa aaggcacggcccaggacccagggaggcgcggggagccaggcctgggc cccgggtccccaagacccttgtgctcgttgtcgccgcggtcctgctg -continued

```
ttggtctcagctgagtctgctctgatcacccaacaagacctagctcc ccagcagagagcggcccacaacaaaagaggtccagcccctcagagg gattgtgtccacctggacaccatatctcagaagacggtagagattgc atctcctgcaaatatggacaggactatagcactcactggaatgacct cctttctgcttgcgctgcaccaggtgtgattcaggtgaagtggagc taagtccctgcaccacgaccagaaacacagtgtgtcagtgcgaagaa ggcaccttccgggaagaagattctcctgagatgtgccggaagtgccg cacagggtgtcccagagggatggtcaaggtcggtgattgtacaccct ggagtgacatcgaatgtgtccacaaagaatcaggtacaaagcacagt ggggaagtcccagctgtggaggagacggtgacctccagcccagggac tcctgcctcttgtgacaaaactcacacatgcccaccgtgccagcac ctgaactcctgggggaccgtcagtcttcctcttcccccaaaaccc aaggacaccctcatgatctcccggacccctgaggtcacatgcgtggt ggtggacgtgagccacgaagaccctgaggtcaagttcaactggtacg tggacggcgtggaggtgcataatgccaagacaaagccgcgggaggag cagtacaacagcacgtaccgtgtggtcagcgtcctcaccgtcctgca ccaggactggctgaatggcaaggagtacaagtgcaaggtctccaaca aagccctcccagcccccatcgagaaaaccatctccaaagccaaggg cagcccgagaaccacaggtgtacaccctgcccccatcccgggatga gctgaccaagaaccaggtcagcctgacctgcctggtcaaaggcttct atcccagcgacatcgccgtggagtgggagagcaatgggcagccggag aacaactacaagaccacgcctcccgtgctggactccgacggctcctt cttcctctacagcaagctcaccgtggacaagagcaggtggcagcagg ggaacgtcttctcatgctccgtgatgcatgaggctctgcacaaccac tacacgcagaagagcctctccctgtctccgggtaaatga
```

LITERATURE

Ahmad, E. I., Gawish, H. H., Al-Azizi, N. M., and El-Hefni, A. M. (2009). The Prognostic Impact of K-RAS Mutations in Adult Acute Myeloid Leukemia Patients Treated with High Dose Cytarabine. Journal of the Egyptian National Cancer Institute 21, 343-350.

Ahn, J., Sanz-Moreno, V., and Marshall, C. J. (2010). The metastasis gene NEDD9 product acts through integrin beta3 and Src to promote mesenchymal motility and inhibit amoeboid motility. J Cell Sci 125, 1814-1826.

Amado, R. G., Wolf, M., Peeters, M., Van Cutsem, E., Siena, S., Freeman, D. J., Juan, T., Sikorski, R., Suggs, S., Radinsky, R., et al. (2008). Wild-type KRAS is required for panitumumab efficacy in patients with metastatic colorectal cancer. Journal of clinical oncology: official journal of the American Society of Clinical Oncology 26, 1626-1634.

Ashkenazi, A., Pai, R. C., Fong, S., Leung, S., Lawrence, D. A., Marsters, S. A., Blackie, C., Chang, L., McMurtrey, A. E., Hebert, A., et al. (1999). Safety and antitumor activity of recombinant soluble Apo2 ligand. J Clin Invest 104, 155-162.

Azijli, K., Weyhenmeyer, B., Peters, G. J., de Jong, S., and Kruyt, F. A. (2013). Non-canonical kinase signaling by the death ligand TRAIL in cancer cells: discord in the death receptor family. Cell death and differentiation 20, 858-868.

Belin de Chantemele, E. J., Retailleau, K., Pinaud, F., Vessieres, E., Bocquet, A., Guihot, A. L., Lemaire, B., Domenga, V., Baufreton, C., Loufrani, L., et al. (2008). Notch3 is a major regulator of vascular tone in cerebral and tail resistance arteries. Arteriosclerosis, thrombosis, and vascular biology 28, 2216-2224.

Bild, A. H., Yao, G., Chang, J. T., Wang, Q., Potti, A., Chasse, D., Joshi, M. B., Harpole, D., Lancaster, J. M., Berchuck, A., et al. (2006). Oncogenic pathway signatures in human cancers as a guide to targeted therapies. Nature 439, 353-357.

Boix-Ferrero, J., Pellin, A., Blesa, J. R., Adrados, M., and Llombart-Bosch, A. (2000). K-ras Gene Mutations in Liver Carcinomas from a Mediterranean Area of Spain. International journal of surgical pathology 8, 267-270.

Chaffer, C. L., and Weinberg, R. A. (2011). A perspective on cancer cell metastasis. Science 331, 1559-1564.

Daniels, R. A., Turley, H., Kimberley, F. C., Liu, X. S., Mongkolsapaya, J., Ch'En, P., Xu, X. N., Jin, B. Q., Pezzella, F., and Screaton, G. R. (2005). Expression of TRAIL and TRAIL receptors in normal and malignant tissues. Cell Res 15, 430-438.

Deschoolmeester, V., Boeckx, C., Baay, M., Weyler, J., Wuyts, W., Van Marck, E., Peeters, M., Lardon, F., and Vermorken, J. B. (2010). KRAS mutation detection and prognostic potential in sporadic colorectal cancer using high-resolution melting analysis. British journal of cancer 103, 1627-1636.

Downward, J. (2003). Targeting RAS signalling pathways in cancer therapy. Nat Rev Cancer 3, 11-22.

Ehrenreiter, K., Kern, F., Velamoor, V., Meissl, K., Galabova-Kovacs, G., Sibilia, M., and Baccarini, M. (2009). Raf-1 addiction in Ras-induced skin carcinogenesis. Cancer cell 16, 149-160.

Ganten, T. M., Koschny, R., Sykora, J., Schulze-Bergkamen, H., Buchler, P., Haas, T. L., Schader, M. B., Untergasser, A., Stremmel, W., and Walczak, H. (2006). Preclinical differentiation between apparently safe and potentially hepatotoxic applications of TRAIL either alone or in combination with chemotherapeutic drugs. Clinical cancer research: an official journal of the American Association for Cancer Research 12, 2640-2646.

Ganten, T. M., Sykora, J., Koschny, R., Batke, E., Aulmann, S., Mansmann, U., Stremmel, W., Sinn, H. P., and Walczak, H. (2009). Prognostic significance of tumour necrosis factor-related apoptosis-inducing ligand (TRAIL) receptor expression in patients with breast cancer. J Mol Med (Berl) 87, 995-1007.

Gao, Y., Dickerson, J. B., Guo, F., Zheng, J., and Zheng, Y. (2004). Rational design and characterization of a Rac GTPase-specific small molecule inhibitor. Proceedings of the National Academy of Sciences of the United States of America 101, 7618-7623.

Gonzalez de Castro, D., Angulo, B., Gomez, B., Mair, D., Martinez, R., Suarez-Gauthier, A., Shieh, F., Velez, M., Brophy, V. H., Lawrence, H. J., et al. (2012). A comparison of three methods for detecting KRAS mutations in formalin-fixed colorectal cancer specimens. British journal of cancer 107, 345-351.

Grady, W. M., and Markowitz, S. D. (2002). Genetic and epigenetic alterations in colon cancer. Annu Rev Genomics Hum Genet 3, 101-128.

Grosse-Wilde, A., Voloshanenko, O., Bailey, S. L., Longton, G. M., Schaefer, U., Csernok, A. I., Schutz, G., Greiner, E. F., Kemp, C. J., and Walczak, H. (2008). TRAIL-R deficiency in mice enhances lymph node metastasis without affecting primary tumor development. J Clin Invest 118, 100-110.

Hanahan, D., and Weinberg, R. A. (2011). Hallmarks of cancer: the next generation. Cell 144, 646-674.

Heid, I., Lubeseder-Martellato, C., Sipos, B., Mazur, P. K., Lesina, M., Schmid, R. M., and Siveke, J. T. (2011). Early requirement of Rac1 in a mouse model of pancreatic cancer. Gastroenterology 141, 719-730, 730 e711-717.

Hidalgo, M. (2010). Pancreatic cancer. The New England journal of medicine 362, 1605-1617.

Hingorani, S. R., Petricoin, E. F., Maitra, A., Rajapakse, V., King, C., Jacobetz, M. A., Ross, S., Conrads, T. P., Veenstra, T. D., Hitt, B. A., et al. (2003). Preinvasive and invasive ductal pancreatic cancer and its early detection in the mouse. Cancer cell 4, 437-450.

Hingorani, S. R., Wang, L., Multani, A. S., Combs, C., Deramaudt, T. B., Hruban, R. H., Rustgi, A. K., Chang, S., and Tuveson, D. A. (2005). Trp53R172H and KrasG12D cooperate to promote chromosomal instability and widely metastatic pancreatic ductal adenocarcinoma in mice. Cancer cell 7, 469-483.

Hoogwater, F. J., Nijkamp, M. W., Smakman, N., Steller, E. J., Emmink, B. L., Westendorp, B. F., Raats, D. A., Sprick, M. R., Schaefer, U., Van Houdt, W. J., et al. (2010). Oncogenic K-Ras turns death receptors into metastasis-promoting receptors in human and mouse colorectal cancer cells. Gastroenterology 138, 2357-2367.

Ito, K., Watanabe, K., Nasim, S., Sasano, H., Sato, S., Yajima, A., Silverberg, S. G., and Garrett, C. T. (1996). K-ras point mutations in endometrial carcinoma: effect on outcome is dependent on age of patient. Gynecologic oncology 63, 238-246.

Jaffee, E. M., Hruban, R. H., Canto, M., and Kern, S. E. (2002). Focus on pancreas cancer. Cancer cell 2, 25-28.

Karapetis, C. S., Khambata-Ford, S., Jonker, D. J., O'Callaghan, C. J., Tu, D., Tebbutt, N. C., Simes, R. J., Chalchal, H., Shapiro, J. D., Robitaille, S., et al. (2008). K-ras mutations and benefit from cetuximab in advanced colorectal cancer. The New England journal of medicine 359, 1757-1765.

Karnoub, A. E., and Weinberg, R. A. (2008). Ras oncogenes: split personalities. Nature reviews Molecular cell biology 9, 517-531.

Kischkel, F. C., Lawrence, D. A., Chuntharapai, A., Schow, P., Kim, K. J., and Ashkenazi, A. (2000). Apo2L/TRAIL-dependent recruitment of endogenous FADD and caspase-8 to death receptors 4 and 5. Immunity 12, 611-620.

Kischkel, F. C., Lawrence, D. A., Tinel, A., LeBlanc, H., Virmani, A., Schow, P., Gazdar, A., Blenis, J., Arnott, D., and Ashkenazi, A. (2001). Death receptor recruitment of endogenous caspase-10 and apoptosis initiation in the absence of caspase-8. The Journal of biological chemistry 276, 46639-46646.

Klein, R. M., Spofford, L. S., Abel, E. V., Ortiz, A., and Aplin, A. E. (2008). B-RAF regulation of Rnd3 participates in actin cytoskeletal and focal adhesion organization. Mol Biol Cell 19, 498-508.

Macher-Goeppinger, S., Aulmann, S., Tagscherer, K. E., Wagener, N., Haferkamp, A., Penzel, R., Brauckhoff, A., Hohenfellner, M., Sykora, J., Walczak, H., et al. (2009). Prognostic value of tumor necrosis factor-related apoptosis-inducing ligand (TRAIL) and TRAIL receptors in renal cell cancer. Clinical cancer research: an official journal of the American Association for Cancer Research 15, 650-659.

Mitsuuchi, Y., and Testa, J. R. (2002). Cytogenetics and molecular genetics of lung cancer. Am J Med Genet 115, 183-188.

Newsom-Davis, T., Prieske, S., and Walczak, H. (2009). Is TRAIL the holy grail of cancer therapy? Apoptosis: an international journal on programmed cell death 14, 607-623.

Ozawa, F., Friess, H., Kleeff, J., Xu, Z. W., Zimmermann, A., Sheikh, M. S., and Buchler, M. W. (2001). Effects and expression of TRAIL and its apoptosis-promoting receptors in human pancreatic cancer. Cancer letters 163, 71-81.

Pan, G., O'Rourke, K., Chinnaiyan, A. M., Gentz, R., Ebner, R., Ni, J., and Dixit, V. M. (1997). The receptor for the cytotoxic ligand TRAIL. Science 276, 111-113.

Phipps, A. I., Buchanan, D. D., Makar, K. W., Win, A. K., Baron, J. A., Lindor, N. M., Potter, J. D., and Newcomb, P. A. (2013). KRAS-mutation status in relation to colorectal cancer survival: the joint impact of correlated tumour markers. British journal of cancer 108, 1757-1764.

Przybojewska, B., Jagiello, A., and Jalmuzna, P. (2000). H-RAS, K-RAS, and N-RAS gene activation in human bladder cancers. Cancer genetics and cytogenetics 121, 73-77.

Sanlioglu, A. D., Koksal, I. T., Ciftcioglu, A., Baykara, M., Luleci, G., and Sanlioglu, S. (2007). Differential expression of TRAIL and its receptors in benign and malignant prostate tissues. The Journal of urology 177, 359-364.

Sanz-Moreno, V., Gadea, G., Ahn, J., Paterson, H., Marra, P., Pinner, S., Sahai, E., and Marshall, C. J. (2008). Rac activation and inactivation control plasticity of tumor cell movement. Cell 135, 510-523.

Scaffidi, C., Medema, J. P., Krammer, P. H., and Peter, M. E. (1997). FLICE is predominantly expressed as two functionally active isoforms, caspase-8/a and caspase-8/b. The Journal of biological chemistry 272, 26953-26958.

Screaton, G. R., Mongkolsapaya, J., Xu, X. N., Cowper, A. E., McMichael, A. J., and Bell, J. I. (1997). TRICK2, a new alternatively spliced receptor that transduces the cytotoxic signal from TRAIL. Current biology: CB 7, 693-696.

Shirasawa, S., Furuse, M., Yokoyama, N., and Sasazuki, T. (1993). Altered growth of human colon cancer cell lines disrupted at activated Ki-ras. Science 260, 85-88.

Spierings, D. C., de Vries, E. G., Timens, W., Groen, H. J., Boezen, H. M., and de Jong, S. (2003). Expression of TRAIL and TRAIL death receptors in stage III non-small cell lung cancer tumors. Clinical cancer research: an official journal of the American Association for Cancer Research 9, 3397-3405.

Sprick, M. R., Rieser, E., Stahl, H., Grosse-Wilde, A., Weigand, M. A., and Walczak, H. (2002). Caspase-10 is recruited to and activated at the native TRAIL and CD95 death-inducing signalling complexes in a FADD-dependent manner but can not functionally substitute caspase-8. The EMBO journal 21, 4520-4530.

Sprick, M. R., Weigand, M. A., Rieser, E., Rauch, C. T., Juo, P., Blenis, J., Krammer, P. H., and Walczak, H. (2000). FADD/MORT1 and caspase-8 are recruited to TRAIL receptors 1 and 2 and are essential for apoptosis mediated by TRAIL receptor 2. Immunity 12, 599-609.

Todaro, M., Lombardo, Y., Francipane, M. G., Alea, M. P., Cammareri, P., Iovino, F., Di Stefano, A. B., Di Bernardo, C., Agrusa, A., Condorelli, G., et al. (2008). Apoptosis resistance in epithelial tumors is mediated by tumor-cell-derived interleukin-4. Cell death and differentiation 15, 762-772.

van Krieken, J. H., Jung, A., Kirchner, T., Carneiro, F., Seruca, R., Bosman, F. T., Quirke, P., Flejou, J. F., Plato Hansen, T., de Hertogh, G., et al. (2008). KRAS mutation testing for predicting response to anti-EGFR therapy for colorectal carcinoma: proposal for an European quality assurance program. Virchows Archiv: an international journal of pathology 453, 417-431.

Varfolomeev, E., Maecker, H., Sharp, D., Lawrence, D., Renz, M., Vucic, D., and Ashkenazi, A. (2005). Molecular determinants of kinase pathway activation by Apo2 ligand/tumor necrosis factor-related apoptosis-inducing ligand. The Journal of biological chemistry 280, 40599-40608.

Walczak, H., Degli-Esposti, M. A., Johnson, R. S., Smolak, P. J., Waugh, J. Y., Boiani, N., Timour, M. S., Gerhart, M. J., Schooley, K. A., Smith, C. A., et al. (1997). TRAIL-R2: a novel apoptosis-mediating receptor for TRAIL. The EMBO journal 16, 5386-5397.

Walczak, H., Miller, R. E., Ariail, K., Gliniak, B., Griffith, T. S., Kubin, M., Chin, W., Jones, J., Woodward, A., Le, T., et al. (1999). Tumoricidal activity of tumor necrosis factor-related apoptosis-inducing ligand in vivo. Nat Med 5, 157-163.

Walsh, A. B., and Bar-Sagi, D. (2001). Differential activation of the Rac pathway by Ha-Ras and K-Ras. The Journal of biological chemistry 276, 15609-15615.

Wegman, P., Ahlin, C., and Sorbe, B. (2011). Genetic alterations in the K-Ras gene influence the prognosis in patients with cervical cancer treated by radiotherapy. International journal of gynecological cancer: official journal of the International Gynecological Cancer Society 21, 86-91.

Wu, G. S., Burns, T. F., Zhan, Y., Alnemri, E. S., and El-Deiry, W. S. (1999). Molecular cloning and functional analysis of the mouse homologue of the KILLER/DR5 tumor necrosis factor-related apoptosis-inducing ligand (TRAIL) death receptor. Cancer research 59, 2770-2775.

---

The invention claimed is:

1. A method for treating an individual with a Kirsten rat sarcoma viral oncogene homologue (KRAS)-mutated cancer, or a cancer in which Rho Associated Coiled-Coil Containing Protein Kinase (ROCK) is inhibited independently of KRAS mutation, the method comprising administering to the individual a therapeutically-effective amount of an agent selected from the group consisting of:
   (i) an agent that binds to and neutralises TNF-related apoptosis-inducing ligand (TRAIL), and
   (ii) an agent that binds to and neutralises TRAIL-receptor 2 (TRAIL-R2).

2. The method of claim 1, wherein the agent is a compound that prevents or inhibits TRAIL from binding to TRAIL-R2 or disrupts a TRAIL/TRAIL-R2 complex resulting from such binding.

3. The method of claim 1, wherein the agent is a compound that binds to and neutralises TRAIL-R2.

4. The method according to claim 3, wherein the compound is an antibody or fragment thereof that binds to and neutralises TRAIL-R2.

5. The method of claim 1, wherein the agent is a compound that binds to and neutralises TRAIL.

6. The method of claim 5, wherein the compound is an antibody or fragment thereof that binds to and neutralises TRAIL.

7. The method of claim 5, wherein the agent is a fusion protein comprising an amino acid sequence selected from the list consisting of:
   (i) the amino acid sequence of SEQ ID NO: 15;
   (ii) the amino acid sequence of SEQ ID NO: 15 lacking the leader peptide:
   MEQRGQNAPAASGARKRHGPGPREARGARPG-PRVPKTLVLVVAAVLLLVSAESAL (amino acids 1-55); and
   (iii) the amino acid sequence of SEQ ID NO: 15 lacking the leader peptide:
   MEQRGQNAPAASGARKRHGPGPREARGARPG-PRVPKTLVLVVAAVLLLVSAESAL (amino acids 1-55) and further lacking up to 5 amino acids from the N-terminus.

8. The method of claim 1, wherein said method inhibits or results in inhibition of Rac1 activity.

9. The method of claim 1, wherein said method inhibits or prevents activation of Rac1 by TRAIL and/or TRAIL-R2 in the KRAS-mutated cancer or cancer in which ROCK is inhibited independently of KRAS mutation.

10. The method of claim 1, the method comprising the steps of
    (i) selecting the individual by identifying the presence of at least one mutation in the KRAS gene in a sample from the individual, and
    (ii) administering a therapeutically effective amount of the agent.

11. The method of claim 10, wherein the individual suffers from a KRAS-mutated cancer, wherein a KRAS gene in the individual is mutated, wherein the mutation in the KRAS gene is selected from Gly12Asp, Gly12Val, Gly13Asp, Gly12Cys, Gly12Ser, Gly12Ala and Gly12Arg, or selected from 12D, 12V, 12C, 12A, 12S, 12R, 12F, 13D, 13C, 13R, 13S, 13A, 13V, 13I, 61H, 61L, 61R, 61K, 61E and 61P.

12. The method of claim 1, wherein said cancer is a human cancer selected from the list consisting of: pancreatic cancer, colorectal cancer, lung cancer, breast cancer, endometrial cancer, cervical cancer, liver cancer, myeloid leukemia, cholangiocarcinoma and bladder cancer.

13. The method of claim 1, wherein the agent is administered in combination with a second therapeutic agent.

14. The method of claim 1, wherein the cancer in which ROCK is inhibited independently of KRAS mutation is one which is associated with aberrant signalling in a pathway selected from: Src, FAK, BRAF, Raf-1, Notch3.

* * * * *